(12) United States Patent
Walthall, Jr. et al.

(10) Patent No.: US 12,150,445 B2
(45) Date of Patent: Nov. 26, 2024

(54) METHOD AND COMPOSITION FOR HYPOTHERMIC STORAGE OF PLACENTAL TISSUE

(71) Applicants: Howard P. Walthall, Jr., Birmingham, AL (US); Katie C. Mowry, Gardendale, AL (US); Jeremy B. Vines, Birmingham, AL (US)

(72) Inventors: Howard P. Walthall, Jr., Birmingham, AL (US); Katie C. Mowry, Gardendale, AL (US); Jeremy B. Vines, Birmingham, AL (US)

(73) Assignee: PRIME MERGER SUB, LLC, Birmingham, AL (US)

( * ) Notice: Subject to any disclaimer, the term of this patent is extended or adjusted under 35 U.S.C. 154(b) by 107 days.

(21) Appl. No.: 17/974,395

(22) Filed: Oct. 26, 2022

(65) Prior Publication Data

US 2023/0077597 A1 Mar. 16, 2023

Related U.S. Application Data

(60) Continuation of application No. 14/972,535, filed on Dec. 17, 2015, which is a division of application No. 14/508,398, filed on Oct. 7, 2014, now abandoned.

(51) Int. Cl.
*A01N 1/02* (2006.01)
*A61K 35/50* (2015.01)
*C12N 5/073* (2010.01)

(52) U.S. Cl.
CPC ......... *A01N 1/0226* (2013.01); *A01N 1/0242* (2013.01); *A01N 1/0263* (2013.01); *A61K 35/50* (2013.01); *C12N 5/0605* (2013.01)

(58) Field of Classification Search
None
See application file for complete search history.

(56) References Cited

U.S. PATENT DOCUMENTS

| | | | |
|---|---|---|---|
| 5,612,028 A | 3/1997 | Sackier | |
| 6,152,142 A | 11/2000 | Tseng | |
| 6,326,019 B1 | 12/2001 | Tseng | |
| 6,548,297 B1 | 4/2003 | Kuri-Harchuch et al. | |
| 6,994,954 B2 | 2/2006 | Taylor | |
| 7,255,879 B2 | 8/2007 | Hariri | |
| 7,488,348 B2 | 2/2009 | Truncale | |
| 8,071,135 B2 | 12/2011 | Liu | |
| 8,153,162 B2 | 4/2012 | Tseng et al. | |
| 8,182,840 B2 | 5/2012 | Tseng et al. | |
| 8,182,841 B2 | 5/2012 | Tseng et al. | |
| 8,187,639 B2 | 5/2012 | Tseng et al. | |
| 8,338,175 B2 | 12/2012 | Devi et al. | |
| 8,354,221 B2 | 1/2013 | Roy et al. | |
| 8,375,688 B2 | 2/2013 | Ishihara et al. | |
| 8,460,650 B2 | 6/2013 | Edinger et al. | |
| 8,932,805 B1 | 1/2015 | Brahm | |
| 9,433,490 B2 | 9/2016 | McFetridge | |
| 9,616,093 B2 | 4/2017 | Tabet et al. | |
| 2003/0187515 A1 | 10/2003 | Hariri et al. | |
| 2003/0235580 A1 | 12/2003 | Zhang | |
| 2004/0048372 A1 | 3/2004 | Hariri | |
| 2005/0196460 A1* | 9/2005 | Malinin | A61L 27/3691 424/548 |
| 2006/0134781 A1 | 6/2006 | Yang | |
| 2007/0128719 A1 | 6/2007 | Tseng | |
| 2007/0231297 A1* | 10/2007 | Smith | A61K 35/50 424/85.1 |
| 2008/0187901 A1 | 8/2008 | Doorschodt et al. | |
| 2008/0193554 A1 | 8/2008 | Dua et al. | |
| 2009/0017438 A1 | 1/2009 | Roy et al. | |
| 2010/0228335 A1 | 9/2010 | Schorgl | |
| 2011/0206776 A1 | 8/2011 | Tom | |
| 2011/0281352 A1 | 11/2011 | Raeder et al. | |
| 2012/0207717 A1 | 8/2012 | Sing | |
| 2013/0071363 A1 | 3/2013 | Smith et al. | |
| 2013/0252226 A1 | 3/2013 | Schweizer | |
| 2013/0084314 A1 | 4/2013 | Horton | |
| 2013/0101562 A1 | 4/2013 | Har-Noy | |
| 2013/0136773 A1 | 5/2013 | Horton et al. | |
| 2013/0195806 A1 | 8/2013 | Gay et al. | |

(Continued)

FOREIGN PATENT DOCUMENTS

CN 102763639 11/2012
CN 103007349 4/2013

(Continued)

OTHER PUBLICATIONS

Francis "Albumin and mammalian cell culture: implications for biotechnology applications" (2010), Cytotechnology, vol. 62: 1-16. (Year: 2010).*
Brockbank K & Taylor MJ. "Tissue Preservation" Advances in Biopreservation, Ch 8, 2006, pp. 159-165.
Hussin et al. "The Fabrication of Human Amniotic Membrane Based Hydrogel for Cartilage Tissue Engineering Applications: A Preliminary Study" Biomed 2011, IFMBE Proceedings 35, pp. 841-844.
Adds, Philip J., et al., Amniotic Membrane Grafts, "Fresh" or Frozen? A Clinical and In Vitro Comparison: BrF Ophthalmol 2001, 85. pp. 905-907.
Xu, L., et al., A Study on the Preservation of Fresh Amniotic Membrane: Yan Ke Xue Bao, Sep. 17, 2001 (3); 158-162.

(Continued)

*Primary Examiner* — Teresa E Knight
(74) *Attorney, Agent, or Firm* — C. Brandon Browning; Maynard Nexsen PC

(57) ABSTRACT

A tissue storage solution includes hypothermic storage compositions and methods. The hypothermic storage composition includes media containing Dulbecco's modified Eagle's medium (DMEM) and albumin. A method of hypothermically storing tissue includes storing such tissue in a storage medium including DMEM and albumin. A method for wound or defect treatment includes applying tissue, stored in a hypothermic storage medium containing DMEM and albumin, to the site of such wound or defect.

16 Claims, 16 Drawing Sheets

(56) References Cited

U.S. PATENT DOCUMENTS

| | | | |
|---|---|---|---|
| 2013/0344163 A1 | 12/2013 | Tseng et al. | |
| 2014/0011743 A1 | 1/2014 | Bhatia et al. | |
| 2014/0017193 A1 | 1/2014 | Sing et al. | |
| 2014/0041403 A1 | 2/2014 | Anderson et al. | |
| 2014/0212390 A1 | 7/2014 | Tabet, Jr. et al. | |
| 2014/0236161 A1 | 8/2014 | Brahm | |
| 2014/0271776 A1 | 9/2014 | Vines et al. | |
| 2015/0079193 A1 | 3/2015 | Yivgi-Ohana | |
| 2015/0342998 A1* | 12/2015 | Tseng | A61L 15/44 424/583 |

FOREIGN PATENT DOCUMENTS

| | | |
|---|---|---|
| CN | 103789262 A1 | 2/2014 |
| JP | H10-509610 A | 9/1998 |
| JP | 2012-116823 A | 6/2012 |
| JP | 2013-010771 A | 1/2013 |
| JP | 2017-514507 A | 6/2017 |
| JP | 2017-514879 A | 6/2017 |
| WO | 2009120996 A1 | 10/2009 |
| WO | 2014057220 A1 | 4/2014 |
| WO | 2015171143 A1 | 11/2015 |
| WO | 2015171144 A1 | 11/2015 |

OTHER PUBLICATIONS

Hennerbichler Simone, et al., The Influence of Various Storage Conditions on Cell Viability in Amniotic Membrane, Cell Tissue Banking (2007) 8:1-8.

Krisnamurthy, et al., "Human amniotic membrane as a chondrocyte carrier vehicle/substrate" In Vitro study 2011. J Biomed Mater Res Part A, vol. 99A: 500-506.

Arora, "Cell Culture Media: A Review" (2013) Mater Methods, vol. 3, No. 175: 1-33.

Campbell, "Preferential uptake of long chain polyunsaturated fatty acids by isolated human placental membranes," Molecular and Cellular Biochemistry, 1996, 155: 77-83.

Gruss et al. "Human amniotic membrane: a versatile wound dressing", CMA Journal, vol. 118, May 20, 1978, pp. 1237-1246.

Burgos et al. "The Maintenance of Human Amniotic membranes in Culture", British Journal of Obstetrics and Gynaecology, vol. 88, Mar. 1981, pp. 294-300.

Examination Report for Australian Patent Application No. 2015328092, mailed on Oct. 18, 2017, 5 Pages.

Examination Report for Australian Patent Application No. 2015328092, mailed on Mar. 21, 2018, 4 Pages.

International Search Report and Written Opinion received for International Patent Application No. PCT/US2015/054494, mailed on Jan. 8, 2016, 17 Pages.

Office Action received for European Patent Application No. 15849362.7, mailed on Apr. 1, 2019, 08 pages.

Extended European Search report received for European Patent Application No. 15849362.7, mailed on Feb. 7, 2018, 18 pages.

Extended European Search report received for European Patent Application No. 22160442.4, mailed on Jun. 10, 2022, 18 pages.

Notice of Refusal for Japanese Patent Application No. 2017-518297, mailed Apr. 3, 2018, 8 Pages including English Translation.

Notice of Refusal for Japanese Patent Application No. 2017-518297, mailed Mar. 5, 2019, 6 Pages including English Translation.

Decision to Grant for Japanese Patent Application No. 2017-518297, mailed Sep. 3, 2019, 5 Pages including English Translation.

International Preliminary Report on Patentability received for International Patent Application No. PCT/US2015/054494, mailed on Apr. 20, 2017, 15 pages.

Search Report received for Japanese Patent Application No. 2017-518297, mailed on Mar. 22, 2018, 27 pages including English translation.

Nikenejad et al., "Properties of the amniotic membrane for potential use in tissue engineering", European Cells and Materials vol. 15, Apr. 2008, pp. 88-99.

Mermet et al., "Use of amniotic membrane transplantation in the treatment of venous leg ulcers", Wound Rep Regen, vol. 15, 2007, pp. 459-464.

Jin et al., "Human Amniotic Membrane as a Delivery Matrix for Articular Cartilage Repair", Tiss Eng, vol. 13, 2007, pp. 693-702.

Moriya et al., "Evaluation of reparative cartilage after autologous chondrocyte implantation for osteochondritis dissecans: histology, biochemistry, and MR imaging", J Orthop Sci, vol. 12, 2007, pp. 265-273.

Mithoefer et al., "Chondral Resurfacing of Articular Cartilage Defects in the Knee with the Microfracture Technique. Surgical Technique", J Bone Joint Surg Am, vol. 88, 2006, pp. 294-304.

Xing et al., "Microfracture combined with osteochondral paste implantation was more effective than microfracture alone for full-thickness cartilage repair", Knee Surg Sports Traumatol Arthrose, vol. 21, 2013, pp. 1770-1776.

Diaz-Prado et al., "Cell Therapy and Tissular Engineering to Regenerate Articular Cartilage", Biomedical Engineering: Trends, Research and Technologies, 2011, pp. 193-216.

Kon et al., "Tissue engineering for total meniscal substitution: animal study in sheep model—results at 12 months", Tissue Eng Part A, vol. 18, Issue 15-16, 2012, pp. 1573-1582.

Fiorentino et al., "Easy and Safe All-Inside Suture Technique for Posterior Horn Tears of Lateral Meniscus Using Standard Anteromedial and Anterolateral Portals", Arthrosc Tech, vol. 2, No. 4, Nov. 2013, pp. e355-e359.

Scotti et al., "Meniscus repair and regeneration: review on current methods and research potential", Eur Cell Mater, vol. 26, 2003, pp. 150-170.

Park et al., "Intervertebral Disk Tissue Engineering Using Biphasic Silk Composite Scaffolds", Tissue Eng Part A, vol. 18, Issue 5-6, 2012, pp. 447-458.

Fuller et al., "Free radical damage and organ preservation: Fact or fiction?: A Review of the interrelationship between oxidative stress and physiological ion disbalance", Cryobiology, vol. 25 issue 5, 1988, pp. 377-393.

Diaz-Prado et al. "Potential use of the human amniotic membrane as a scaffold in human articular cartilage repair", Cell Tissue Bank, vol. 11, 2010, 13 Pages.

* cited by examiner

DMEM + rhA 42 days

DMEM supplemented 29 days

DMEM 19 days

† p < 0.01 to average at day 1
** p < 0.05
* p < 0.01
# p < 0.001

FIG. 5A  FIG. 5B  FIG. 5E
4 weeks
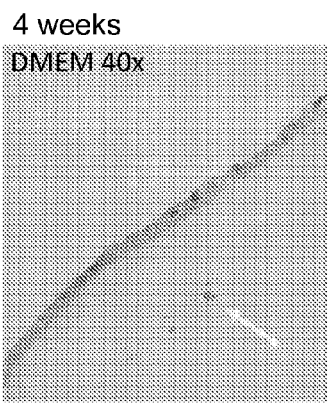
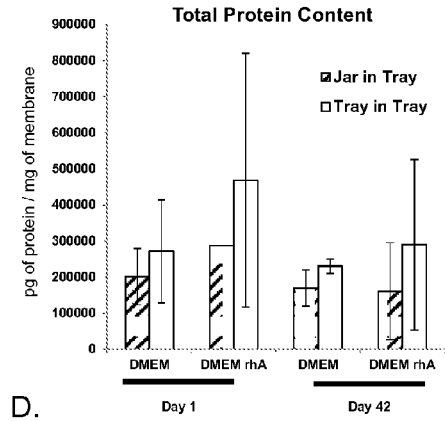
B. 6 weeks
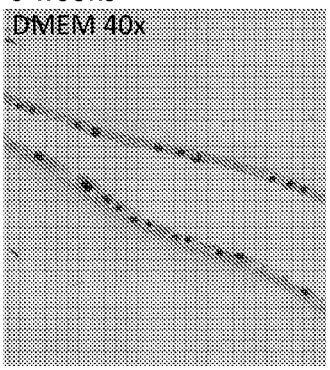  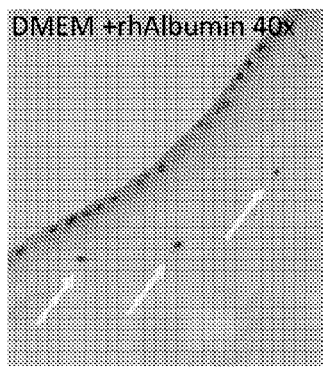
D.
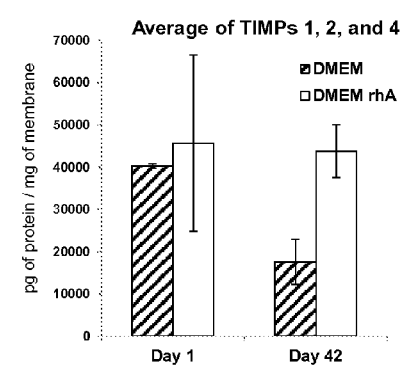
FIG. 5C  FIG. 5D  FIG. 5F

3 animals/9 days post-op

9 Days Histological Evaluation Summary

Fresh Stored Membrane Evaluation
- Large surgical wound/scar
- More cellular granulation tissue
- some better re-epithelialization (compared to control)
- Some vascularity

Dehydrated Mesh Evaluation
- Large surgical wound/scar
- More cellular granulation tissue
- some re-epithelialization
- Some vascularity

Dehydrated Amnion Evaluation
- Large surgical wound/scar
- Granulation tissue
- 1 of 3 with some re-epithelialization
- Some vascularity

Control Evaluation
- Large surgical wound
- Scar
- Granulation tissue
- Some vascularity

FIG. 8

4 animals/21 days post-op

21 Days Histological Evaluation Summary

Fresh Stored Membrane Evaluation
- ↑↑ wound healing
- ↑ increased collagen deposition
- Normal skin architecture
- Extensive hair follicles/sebaceous glands (3 of 4)
- Completely re-epithelialized

More Healing/ Mature wound resolving

Dehydrated Mesh Evaluation
- Broad based wound
- More cellular granulation tissue
- Completely re-epithelialized
- normal vascularity

No Consistent Differences

Dehydrated Amnion Evaluation
- Broad based wound
- Good granulation tissue
- Completely re-epithelialized
- Mild collagen deposition in some
- Early hair formation in margins in some
- Normal vascularity

Mildly better than Control

Control Evaluation
- Broad based wound
- Good granulation tissue
  - Not as cellular
  - More cellular deep in tissue/patchy
- No collagen in-growth
- Completely re-epithelialized
- ¼ have beginning of hair follicle development

FIG. 10

4 animals/21 days post-op
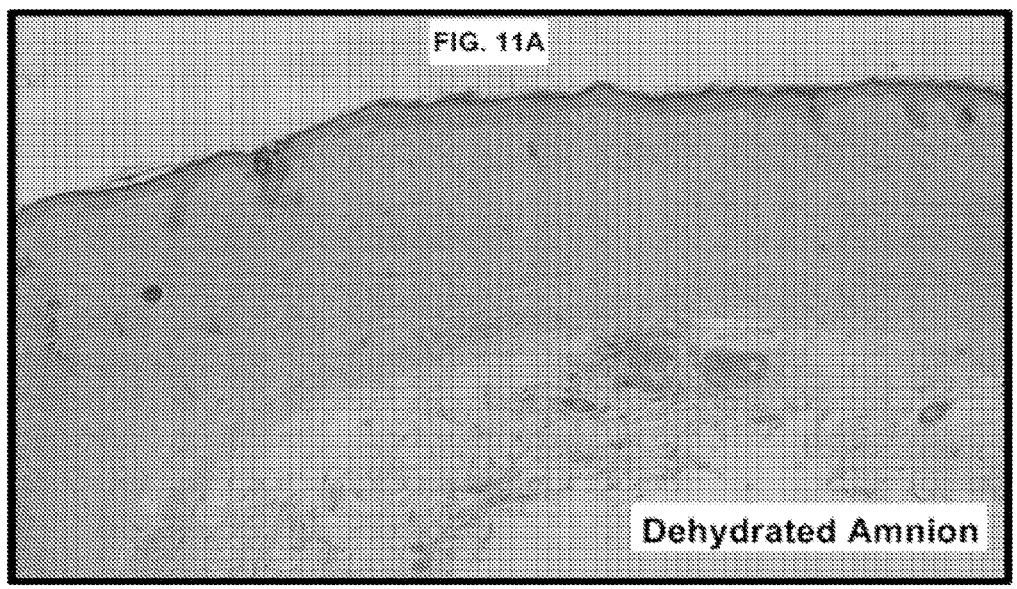
FIG. 11A Dehydrated Amnion
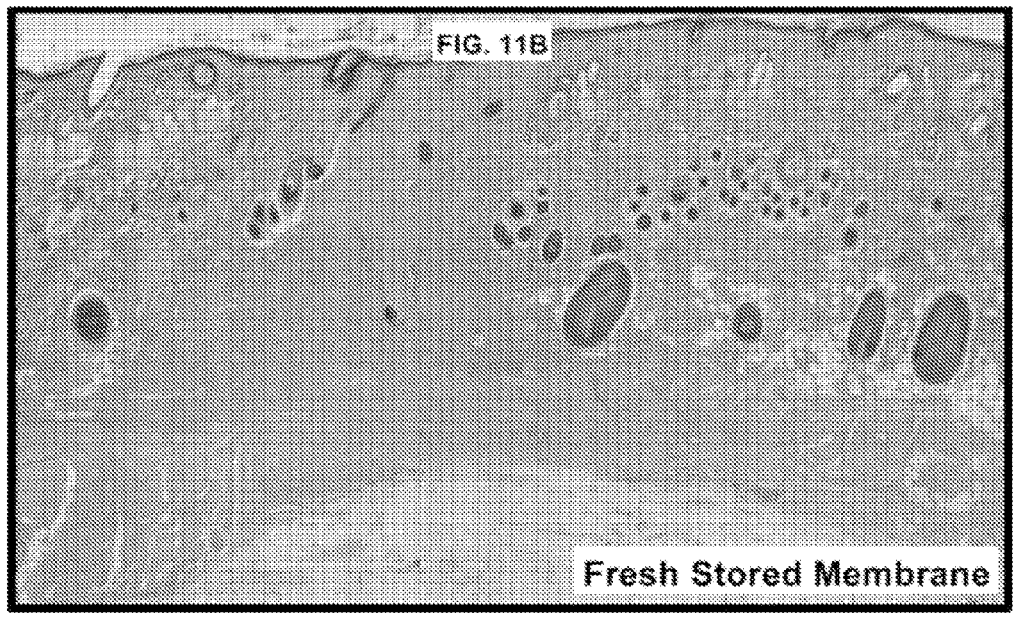
FIG. 11B Fresh Stored Membrane 4 animals/21 days post-op

FIG. 11C

Control

FIG. 11D

Dehydrated Meshed

4 animals/21 days post-op
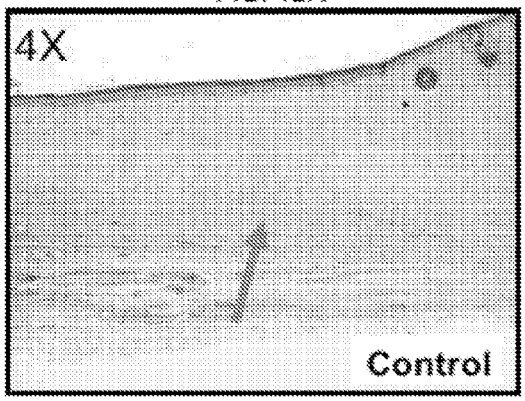
FIG. 12A — Control
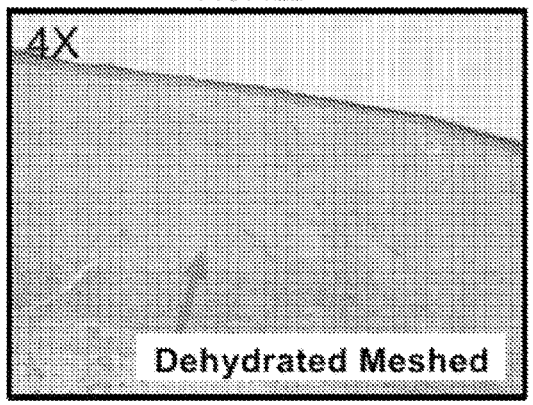
FIG. 12B — Dehydrated Meshed
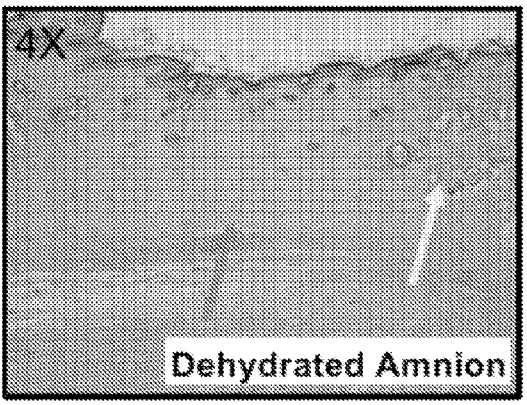
FIG. 12C — Dehydrated Amnion
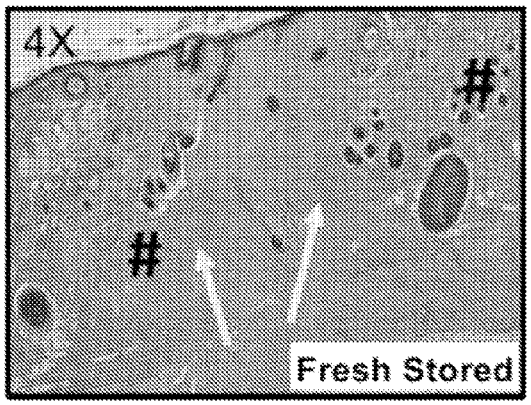
FIG. 12D — Fresh Stored
- # - Follicle and sebaceous gland development
- Yellow Arrows – New collagen deposition/ reparative tissue
- Blue Arrows -- Granulation tissue

METHOD AND COMPOSITION FOR HYPOTHERMIC STORAGE OF PLACENTAL TISSUE

RELATED APPLICATIONS

This application is a continuation of and claims priority to U.S. patent application Ser. No. 14/972,535 for "Method and Composition for Hypothermic Storage of Placental Tissue," filed on Dec. 17, 2015, the entire contents of which are incorporated herein by reference. U.S. patent application Ser. No. 14/508,398 is a divisional of and claims priority to U.S. patent application Ser. No. 14/508,398 for "Method and Composition for Hypothermic Storage of Placental Tissue," filed on Oct. 7, 2014, the entire contents of which are incorporated herein by reference.

FIELD OF THE INVENTION

The present invention is directed to hypothermic storage compositions and methods. More particularly, the present invention is directed to a hypothermic storage solution including Dulbecco's modified Eagle's medium (DMEM) and human plasma albumin, a method of hypothermically storing tissue, such as placental membrane, in the solution, and a method for wound treatment by applying tissue stored in the solution to the site of a wound.

BACKGROUND OF THE INVENTION

The placenta surrounds a fetus during gestation and is composed of, among other tissues, an inner amniotic layer that faces the fetus and a generally inelastic outer shell, or chorion. The placenta anchors the fetus to the uterine wall, allowing nutrient uptake, waste elimination, and gas exchange to occur via the mother's blood supply. Additionally, the placenta protects the fetus from an immune response from the mother. From the placenta, an intact placental membrane comprising the amnion and chorion layers can be separated from the other tissues. The amnion is the innermost layer of the placenta and consists of a thick basement membrane and an avascular stromal matrix.

Clinicians have used intact placental membrane, comprising an amnion and a chorion layer, in medical procedures since as early as 1910 [Davis J. S., *John Hopkins Med J*, 15:307 (1910)]. The amniotic membrane, when separated from the intact placental membrane, may also be used for its beneficial clinical properties [Niknejad H., et al. *Eur Cell Mater*, 15:88-99 (2008)]. Certain characteristics of the placental membrane make it attractive for use by the medical community. These characteristics include, but are not limited to: its anti-adhesive, anti-microbial, and anti-inflammatory properties; wound protection; its ability to induce epithelialization; and pain reduction [Mermet I., et al. *Wound Rep Regen*, 15:459 (2007)].

Other uses for placental membrane include its use for scaffolding or providing structure for the regrowth of cells and tissue. An important advantage of placental membrane in scaffolding is that the amnion contains an epithelial layer. The epithelial cells derived from this layer are similar to stem cells, allowing the cells to differentiate into cells of the type that surrounds them. Multipotent cells similar to stem cells are also contained within the body of the amniotic membrane. Additionally, the amniotic membrane contains various growth and trophic factors, such as epidermal, insulin-like, and fibroblast growth factors, as well as high concentrations of hyaluronic acid, which may be beneficial to prevent scarring and inflammation and to support healing. Thus, placental membrane offers a wide variety of beneficial medical uses.

Cell-based therapies have considerable potential for the repair and regeneration of tissues. The addition of a scaffold to these cell-based therapies has yielded improved outcomes [Krishnamurithy G., et al. *J Biomed Mater Res Part A*, 99A:500-506 (2011)]. Ideally, the material used for the scaffold will be biocompatible such that it provokes little to no immune response, biodegrades, and is available in sufficient quantities to be practical. Although the placental membrane has long been identified as a material potentially filling this role in the clinic, efforts have been limited to in vitro studies, impractical in vivo techniques, or have yielded less-than-optimal outcomes. Furthermore, the conditions under which the scaffold is used may have a dramatic effect on the therapeutic efficacy.

A number of placental membrane products have been studied in the literature and used clinically, falling into two primary categories. The first category involves the use of the intact membrane, be it fresh, dried, freeze-dried, cryopreserved, or preserved in glycerol or alcohol. In this formulation, the membrane is useful for a number of purposes, but is not suitable for others, such as applications requiring injection, or the filling of a space which does not conform to the thin planar shape of the membrane itself.

The second category involves the grinding, pulverizing and/or homogenizing of the membrane into small particles, which may then be resuspended in solution. Such techniques are described, for example, in U.S. patent application Ser. Nos. 11/528,902; 11/528,980; 11/529,658; and Ser. No. 11/535,924. This grinding may be done dry or wet, and temperature during grinding may or may not be controlled, such as in the case of cryogrinding. Products produced using this method are useful for a number of applications, and may be injected under appropriate conditions. However, they have several deficiencies for certain applications. First, the cells contained in the placental membranes will be destroyed during the grinding process. Second, proteins and growth factors in the membrane may be leached out or lost during this process, including any subsequent washing or other treatment of the ground particles. Indeed, the removal of potentially angiogenic factors such as growth factors may be an objective of this type of processing. Third, resuspension of these small particles in typical physiologic solutions, such as saline, results in a free-flowing fluid with low viscosity. Upon injection or placement, this fluid may dissipate rather than remain in the desired treatment location. Fourth, the resulting fragments may not be large enough to permit cell engraftment and proliferation, if so desired.

However, amniotic membrane preparations have been shown to have significant beneficial bioactivity. Many of the cells contained in these membranes are multi- or pluripotent. The membranes also contain a rich source of growth factors, as well as hyaluronic acid, collagen, and other factors which have been shown to support tissue healing. Amniotic membrane has been shown to attract and to stimulate the proliferation of cells involved in tissue healing, such as mesenchymal stem cells (MSCs) and fibroblasts.

Articular cartilage, located on the articular ends of bones at joints throughout the body, is composed of hyaline cartilage and contains relatively few chondrocytes that are embedded in extracellular matrix materials, such as type II collagen and proteoglycans [Moriya T., et al. *J Orthop Sci*, 12:265-273 (2007)]. Articular cartilage has a limited ability to self-repair, in part due to the avascular characteristics of the cartilage, which poses a significant challenge to treating joint injuries and diseases. The repair of cartilage defects in humans can therefore be a difficult endeavor, and multiple options exist for the surgeon to treat such defects. The surgeon may choose to influence the defect with microfracture, abrasion or other marrow stimulation techniques which stimulate bleeding of the subchondral bone and the generation of a clot and ultimately a fibrocartilage patch which fills the defect. Other options allow for the filling of the defect with chondrocytes of variable sources, both of autograft and allograft origin.

A key advantage of marrow stimulation techniques over most other available therapies is that marrow stimulation may be carried out arthroscopically using a relatively simple surgical technique, with minimal disruption to the joint and surrounding tissues [Mithoefer K., et al. *J Bone Joint Surg Am*, 88(Suppl 1 Pt 2):294-304 (2006)]. The technique is also cost-effective. Efforts have therefore been made to improve the outcome of marrow stimulation techniques. Ground cartilage, either autograft or allograft (e.g. the product commercially marketed as BioCartilage), has been proposed for this purpose [Xing L., et al. *Knee Surg Sports Traumatol Arthrosc*, 21:1770-1776 (2013)]. However the use of autograft cartilage requires additional operative steps and donor site morbidity. Further, the use of allograft cartilage alone has not yielded satisfactory results.

Current treatments, including cell-based therapies, have resulted in the generation of undesirable fibro cartilaginous tissue rather than hyaline cartilage [Diaz-Prado S. M., et al. BIOMEDICAL ENGINEERING, TRENDS, RESEARCH, AND TECHNOLOGIES, pp. 193-216 (2011)]. As such, there remains a significant clinical need for therapies capable of repairing damaged articular cartilage by specifically regenerating hyaline-like cartilage.

A similar need exists for solutions for the repair of meniscal defects. A meniscus is a crescent-shaped fibrocartilaginous structure that, in contrast to articular discs, only partly divides a joint cavity. In humans they are present in the knee, acromioclavicular, sternoclavicular, and temporomandibular joints. Generally, the term 'meniscus' refers to the cartilage of the knee, either to the lateral or medial menisci. Both are cartilaginous tissues that provide structural integrity to the knee as it undergoes tension and torsion. They are concave on the top and flat on the bottom, articulating with the tibia. They are attached to the small depressions (fossae) between the condyles of the tibia (intercondyloid fossa), and towards the center they are unattached and their shape narrows to a thin shelf. The blood flow of the meniscus is from the periphery to the central meniscus. Blood flow decreases with age and the central meniscus is avascular by adulthood leading to very poor healing rates. Meniscal defects are repaired using sutures or other fixation approaches. Partial meniscectomies are also commonly used [Kon E., et al. *Tissue Eng Part A*, 18(15-16):1573-1582 (2012); Fiorentino G., et al. *Arthrosc Tech*, 2(4):e355-e359 (2013); Scotti C., et al. *Eur Cell Mater*, 26:150-170 (2013)].

Another related problem involves the regeneration of the human intervertebral disc. Intervertebral discs are fibrocartilaginous tissues occupying the space between vertebral bodies in the spine. They transmit forces from one vertebra to the next, while allowing spinal mobility. The structural properties of the disc are largely dependent on its ability to attract and to retain water. Proteoglycans in the disc exert an osmotic "swelling pressure" that resists compressive loads. Degeneration of the intervertebral disc is a physiologic process that is characteristic of aging in humans. With age, the disc undergoes a variety of changes, the most notable being a loss of proteoglycan content resulting in reduced osmotic pressure and a reduction in disc height and ability to transmit loads [Park S. H., et al., *Tissue Eng Part A*, 18(5-6):447-458 (2012)]. Disc degeneration is an important and direct cause of spinal conditions that account for most neck and back pain. As is the case with the related cartilage cells, components of the amniotic membrane may promote healing and recovery of the intervertebral disc and associated cells.

The storage and transport of placental membranes are subject to numerous regulatory schemes. For example, the membranes must be stored for a specific period of time before use in a subject (i.e., fourteen days before use), during which time it is periodically tested for contamination from bacteria, viruses and other non-placental cell types. Additional delay is caused by the transport of the membrane to the appropriate medical facility. This delay may reduce viability of the placental membrane cells. To maintain cell viability within the amniotic membrane, it must be stored and transported in cell culture media containing appropriate supplements. These supplements should be selected to maximize cell viability and to extend the time in which the tissue can be reliably stored. The membrane storage media should meet currently existing clinical standards to guarantee the safety of the products and ensure regulatory compliance. The media therefore must be chemically defined/cGMP compliant and must be free of both xeno-derived and human-derived components.

Traditional tissue storage generally involves cryogenic preservation methods by which cells or whole tissues are preserved by cooling to sub-zero temperatures. The low temperatures effectively stop any enzymatic or chemical activity that might cause tissue damage. Cryopreservation methods seek to reach low temperatures without causing additional damage by the formation of ice during freezing. Traditional cryopreservation techniques rely on coating the cells or tissues with a cryoprotectant to prevent intracellular ice formation. Macroscopic ice formation may still occur, however, causing perforation which affects the integrity of the tissue.

Hypothermic tissue storage generally occurs at temperatures above freezing, for instance from between 0° C. and 20° C., which prevents ice crystal formation. Many issues relating to cell function and viability are associated with hypothermic tissue storage, such as osmolality, ischemia, hypoxia, and oxygen-derived free radicals, as described below.

Osmolality. Under equilibrium, a higher concentration of inorganic ions are present in the intracellular space as opposed to the extracellular space, a phenomenon known as the Donna Effect [Dick, D. A. T., *Relation between water and solutes: Theory of osmotic pressure*, in CELL WATER, E. E. Bittar, Editor 1966, Butterworths: London. pp. 15-43.]. Therefore, at equilibrium, there is a tendency for cells to uptake water. Cells manage their osmolality via active ion transport in which ions, such as sodium and chloride, are transported out of the membrane via pumps to prevent water intake and subsequent lysis. Osmolality is a colligative property and dependent on the amount of ions present within solution as opposed to their size or nature [Taylor M. J., *Physico-chemical principles in low temperature biology*, in THE EFFECTS OF LOW TEMPERATURES ON BIOLOGICAL SYSTEMS, B. W. W. Grout & G. J. Morris, Editors. 1987, Edward Arnold: London. pp. 3-71.]. The ATP consumption required to perform the active transport reactions are adapted to occur at normal body temperature. At hypothermic temperatures, the active transport pumps are unable to bind to ATP to process it as energy. In addition, under hypothermic conditions, high energy reserves are depleted when mitochondrial energy transduction (production of ATP) fails. The activity of the sodium and potassium pumps at 5° C. is approximately 1% of its normal levels at physiological temperatures [Ellory J. C. & Willis J. S., *Phasing out the sodium pump*, in EFFECTS OF LOW TEMPERATURES ON BIOLOGICAL MEMBRANES, G. J. Morris and A. Clarke, Editors. 1981, Academic Press: London. pp. 107-120.]. Normal osmolality of the extracellular fluid is approximately 280 to 310 mOsmol/L. Because the sodium and potassium pumps fail under hypothermic conditions, hypothermic storage media should be slightly hypertonic to counteract this change.

Ischemia/Hypoxia. An immediate consequence of cessation of blood supply to an organ is the loss of oxygen supply to the tissue. Oxygen is necessary for the process of aerobic respiration and the production of adenosine triphosphate (ATP), the main energy source utilized by cells. In the absence of oxygen, ATP is depleted within a few minutes. This depletion leads to a shift from aerobic to anaerobic metabolism which is self-limiting and causes the production of lactate and protons. This leads to a cascade eventually culminating in necrosis and cell death.

For every 10° C. drop in temperature, cellular oxygen consumption declines 50% [Taylor M. J., *Biology of Cell Survival in the Cold: The Basis for Biopreservation of Tissues and Organs*, in ADVANCES IN BIOPRESERVATION, J. G. Baust & J. M. Baust, Editors. 2007, CRC Press: Boca Raton, FL]. This produces slower reaction rates and a decrease in cellular metabolism.

Oxygen-derived free radicals (ODFRs). The cooling of cells increases their susceptibility to produce free radicals while attenuating the mechanisms by which cells normally deal with free radical formation [Fuller B. J., Gower J. D., & Green C. J., *Cryobiology,* 25(5):377-393 (1988)]. Low concentrations of molecular oxygen, such as those found in tissue preservation solutions, are sufficient for the development of ODFRs. For this reason, natural pharmacological scavengers such as SOD, catalase, or mannitol may improve the viability of hypothermically stored organs [Fuller, et al. *Cryobiology,* 23(4):358-365(1986)].

SUMMARY OF THE INVENTION

The present invention is directed to both compositions and methods related to the hypothermic storage of tissue. According to one aspect of the invention, there is provided a composition of hypothermic storage media that includes DMEM and albumin. In another aspect of the invention, there is provided a method of hypothermically storing tissue. The method includes the steps of preparing or obtaining media containing DMEM and albumin, placing tissue into the media, and storing the tissue and media hypothermically. In yet another aspect of the invention there is provided a method for wound treatment. The method includes the steps of storing tissue in hypothermic storage media and applying the tissue to the site of the wound. The tissue may also be minced or ground into particles, which may be injected into the site of the wound.

A further understanding of the nature and advantages of the present invention will be realized by reference to the remaining portions of the specification and the drawings of the present application.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

FIG. 5A is an illustration of histological staining of tissues stored in a DMEM solution for four weeks.

FIG. 5B is an illustration of histological staining of tissues stored in a DMEM+rhA solution for four weeks.

FIG. 5C is an illustration of histological staining of tissues stored in a DMEM solution for six weeks.

FIG. 5D is an illustration of histological staining of tissues stored in a DMEM+rhA solution for six weeks.

FIG. 5E is a graph illustrating the total protein content of placental membrane cells.

FIG. 5F is a graph illustrating the concentration of tissue inhibiting matrix metalloproteinases in placental membrane cells.

FIG. 8 is a chart listing the results of the histological examination of wounds treated with experimental placental membranes nine days post-procedure.

FIG. 10 is a chart listing the results of the histological examination of wounds treated with experimental placental membranes twenty-one days post-procedure.

FIG. 11A is an illustration of the histological examination of a wound treated with dehydrated amnion twenty-one days post-procedure.

FIG. 11B is an illustration of the histological examination of a wound treated with fresh hypothermically stored placental membrane twenty-one days post-procedure.

FIG. 11C is an illustration of the histological examination of an untreated wound twenty-one days post-procedure.

FIG. 11D is an illustration of the histological examination of a wound treated with dehydrated mesh twenty-one days post-procedure.

FIG. 12A is an additional illustration of the histological examination of a wound treated with dehydrated mesh twenty-one days post-procedure.

FIG. 12B is an additional illustration of the histological examination of a wound treated with dehydrated mesh twenty-one days post-procedure.

FIG. 12C is an additional illustration of the histological examination of a wound treated with dehydrated amnion twenty-one days post-procedure.

FIG. 12D is an additional illustration of the histological examination of a wound treated with dehydrated amnion twenty-one days post-procedure.

DETAILED DESCRIPTION OF THE INVENTION

Figure 1A:
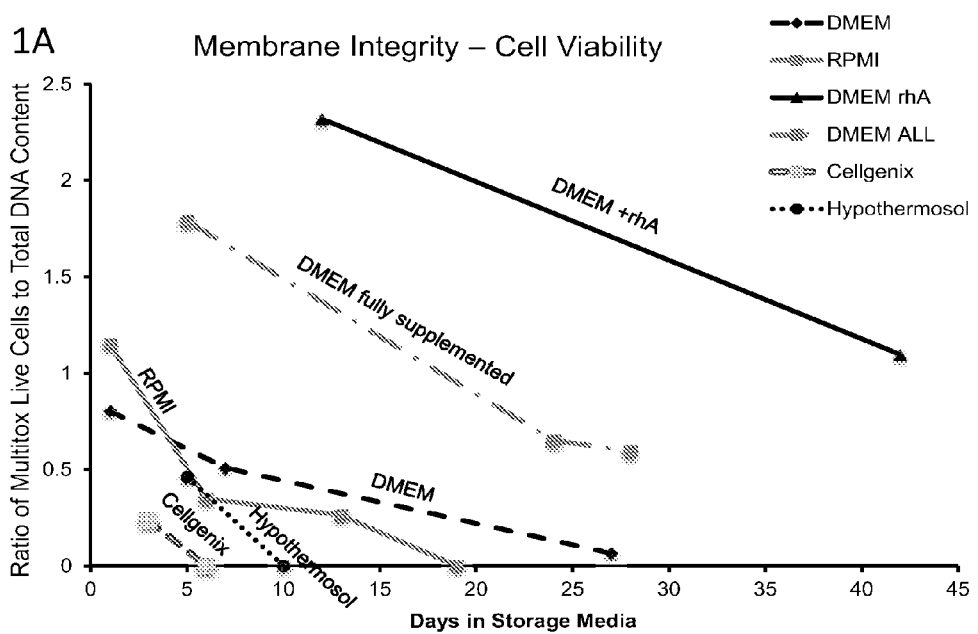
FIG. 1A is a graph illustrating preliminary cell viability assessment.

Before the present compositions, articles, devices, and/or methods are disclosed and described, it is to be understood that they are not limited to specific methods unless otherwise specified, or to particular reagents unless otherwise specified, and as such may vary. It is also to be understood that the terminology as used herein is used only for the purpose of describing particular embodiments and is not intended to be limiting.

This application references various publications. The disclosures of these publications, in their entireties, are hereby incorporated by reference into this application to describe more fully the state of the art to which this application pertains. The references disclosed are also individually and specifically incorporated herein by reference for material contained within them that is discussed in the sentence in which the reference is relied on.

A. Definitions

In this specification, and in the claims that follow, reference is made to a number of terms that shall be defined to have the following meanings:

As used herein, the singular forms "a," "an," and "the" include plural referents unless the context clearly indicates otherwise. Thus, for example, reference to "the wound" includes two or more such wounds, and the like.

As used herein, ranges can be expressed as from "about" one particular value, and/or to "about" another particular value. When such a range is expressed, an embodiment includes from the one particular value and/or to the other particular value. Similarly, when values are expressed as approximations, by the use of "about," it will be understood that the particular value forms another embodiment. It will be understood that the endpoints of each of the ranges are significant both in relation to the other endpoint and independently of the other endpoint. It will also be also understood that there are a number of values disclosed herein, and that each value is also disclosed herein as "about" that particular value in addition to the value itself. For example, if the value "50" is disclosed, then "about 50" is also disclosed. It is also understood that when a value is disclosed that "less than or equal to" a value, that values "greater than or equal to the value" and possible ranges between values are also disclosed, as understood by one skilled in the art. For example, if the value "50" is disclosed, then "less than or equal to 50" and "greater than or equal to 50" are also disclosed. It is also understood that the throughout the application, data are provided in different formats, and it is understood that these data represent endpoints and starting points as well as ranges for any combination of the data points. For example, if a particular data point "50" and a particular data point "100" are disclosed, it is understood that greater than, greater than or equal to, less than, less than or equal to, and equal to 50 and 100 are considered disclosed as well as between 50 and 100.

As used herein, "amniotic tissue" means amniotic fluid cells, placental membrane, amnion tissue or combinations thereof.

As used herein, the terms "optional" and "optionally" mean that the subsequently described event or circumstance may or may not occur, and that the description includes instances where said event or circumstance occurs and instances where it does not occur.

As used herein, the phrase "substantially all" refers to the maximum amount reasonably attainable by one skilled in the art.

As used herein, the phrases "placental membrane" and "amnion tissue" refer to one or more layers of the placental membrane. For example, placental membrane or amnion tissue may refer to a placental membrane comprising both the amniotic and chorionic layers. In another example, placental membrane or amnion tissue may refer to a placental membrane in which the chorion has been removed. In another example, placental membrane or amnion tissue may refer to a placental membrane in which the epithelial layer has been removed.

As used herein, the terms "treatment" and "treating" include any desirable effect on the symptoms or pathology of a disease or condition, and may include even minimal reductions in one or more measurable markers of the disease or condition being treated. "Treatment" does not necessarily indicate complete eradication or cure of the disease or condition, or associated symptoms thereof. The subject receiving this treatment is any animal in need, including primates, in particular humans, and other mammals including, but not limited to, equines, cattle, swine, sheep, poultry and pets in general.

B. Making of the Placental Membrane Preparation

The placental membranes that utilize the present hypothermic storage solution may be prepared as described previously in U.S. patent application Ser. No. 14/212,010, entitled "Preparations Derived From Placental Materials and Methods of Making and Using the Same," U.S. patent application Ser. No. 13/754,742, entitled "Placental Membrane Preparation and Methods of Making and Using the Same," and U.S. patent application Ser. No. 13/754,716, entitled "Placental Membrane Preparation and Methods of Making and Using the Same," the contents of which are incorporated herein by reference. Briefly, the placental membrane preparation includes amnion tissue and, optionally, amniotic fluid cells. The amnion tissue component of the placental membrane preparation is produced from placentas collected from consenting donors in accordance with the Current Good Tissue Practice guidelines promulgated by the U.S. Food and Drug Administration. In particular, soon after the birth of a human infant via a Cesarean section delivery, the intact placenta is retrieved, and the placental membrane is dissected from the placenta. Afterwards, the placental membrane is cleaned of residual blood, placed in a bath of sterile solution, stored on ice and shipped for processing. Once received by the processor, the placental membrane is rinsed to remove any remaining blood clots, and if desired, rinsed further in an antibiotic rinse [Diaz-Prado S. M., et al. *Cell Tissue Bank*, 11:183-195 (2010)].

The antibiotic rinse may include, but is not limited to, the antibiotics: amikacin, aminoglycosides, amoxicillin, ampicillin, ansamycins, arsphenamine, azithromycin, azlocillin, aztreonam, bacitracin, capreomycin, carbacephem, carbapenems, carbenicillin, cefaclor, cefadroxil, cefalexin, cefalotin, cefamandole, cefazolin, cefdinir, cefditoren, cefepime, cefixime, cefoperazone, cefotaxime, cefoxitin, cefpodoxime, cefprozil, ceftaroline fosamil, ceftazidime, ceftibuten, ceftizoxime, ceftobiprole, ceftriaxone, cefuroxime, chloramphenicol, ciprofloxacin, clarithromycin, clindamycin, clofazimine, cloxacillin, colistin, cycloserine, dapsone, daptomycin, demeclocycline, dicloxacillin, dirithromycin, doripenem, doxycycline, enoxacin, ertapenem, erythromycin, ethambutol, ethionamide, flucloxacillin, fosfomycin, furazolidone, fusidic acid, gatifloxacin, geldanamycin, gentamicin, glycopeptides, grepafloxacin, herbimycin, imipenem or cilastatin, isoniazid, kanamycin, levofloxacin, lincomycin, lincosamides, linezolid, lipopeptide, lomefloxacin, loracarbef, macrolides, mafenide, meropenem, methicillin, metronidazole, mezlocillin, minocycline, monobactams, moxifloxacin, mupirocin, nafcillin, nalidixic acid, neomycin, netilmicin, nitrofurans, nitrofurantoin, norfloxacin, ofloxacin, oxacillin, oxytetracycline, paromomycin, penicillin G, penicillin V, piperacillin, platensimycin, polymyxin B, pyrazinamide, quinolones, quinupristin/dalfopristin, rifabutin, rifampicin or rifampin, rifapentine, rifaximin, roxithromycin, silver sulfadiazine, sparfloxacin, spectinomycin, spiramycin, streptomycin, sulfacetamide, sulfadiazine, sulfamethizole, sulfamethoxazole, sulfanilamide, sulfasalazine, sulfisoxazole, sulfonamidochrysoidine, teicoplanin, telavancin, telithromycin, temafloxacin, temocillin, tetracycline, thiamphenicol, ticarcillin, tigecycline, tinidazole, tobramycin, trimethoprim, trimethoprim-sulfamethoxazole (co-trimoxazole) (TMP-SMX), and troleandomycin, trovafloxacin, or vancomycin.

The antibiotic rinse may also include, but is not limited to, the antimycotics: abafungin, albaconazole, amorolfin, amphotericin B, anidulafungin, bifonazole, butenafine, butoconazole, caspofungin, clotrimazole, econazole, fenticonazole, fluconazole, isavuconazole, isoconazole, itraconazole, ketoconazole, micafungin, miconazole, naftifine, nystatin, omoconazole, oxiconazole, posaconazole, ravuconazole, sertaconazole, sulconazole, terbinafine, terconazole, tioconazole, voriconazole, or other agents or compounds with one or more anti-fungal characteristics.

Although placental membranes possess many benefits and applications, availability of the membranes has limited their use. The amount of placental membrane generated from a single birth is small. As would be expected, because the supply of placental membranes is relatively small, the cost of placental membranes limits their use only to procedures that surpass a certain price or complexity. U.S. patent application Ser. Nos. 13/250,096 and 13/647,525 describe a placental membrane including a plurality of slits for increasing the membranes capacity to expand. The slits are provided through the membrane and are provided in sufficient numbers to produce a mesh-like pattern which enables the membrane to be stretched and therefore increase its length and width.

The placental membrane may be processed to remove one or more particular layers of the membrane. The chorion may be removed from the placental membrane by mechanical means well-known to those skilled in the art. The chorion may be removed, for example, by carefully peeling the chorion from the remainder of the placental membrane using blunt dissection [Jin C. Z., et al. *Tiss Eng*, 13:693-702 (2007)]. Removal of the epithelial layer from the placental membrane may be achieved using several methods well-known to those skilled in the art. The epithelial layer may be preserved or, if desired, may be removed by, for example, using trypsin to induce necrosis in the epithelial cells [Diaz-Prado S. M., et al. *Cell Tissue Bank*, 11:183-195 (2010)]. Removal of the epithelial layer may comprise, for example, treatment with 0.1% trypsin-ethylenediaminetetraacetic acid (EDTA) solution at 37° C. for 15 minutes followed by physical removal using a cell scraper [Jin C. Z., et al. *Tiss Eng*, 13:693-702 (2007)]. Preferably, the placental membrane utilized for the amnion tissue component of the placental membrane preparation is the amniotic membrane including the amniotic epithelial cell layers but excluding the chorion.

The placental membranes may be ground using techniques known in the art, and the resulting particles either re-suspended in the hypothermic storage medium described herein or dried. Such processing may be carried out so as to preserve, to the extent possible, the protein content of the membrane, including growth factors. Preferably, grinding should be conducted under temperature-controlled conditions, such as in a cryomill. Preferably such ground pieces of tissue should have a particle size of less than 1 mm. Alternatively, the membranes may be minced using techniques known in the art, creating, for example, small cubes of membrane tissue. Preferably such minced pieces of tissue have particle sizes ranging from 0.1 mm to 5 mm. Minced tissue particles may be square, rounded, oblong or irregular in shape.

The ground or minced placental membrane includes amnion tissue containing organized amniotic extracellular matrix (ECM), amniotic tissue cells and growth factors contained within the ECM and amniotic tissue cells. The ECM includes amnion-derived collagen, fibronectin, laminin, proteoglycans and glycosaminoglycans. The amnion-derived collagen may be derived from an epithelium layer, a basement membrane layer, a compact layer, a fibroblast layer, an intermediate layer and a spongy layer of the amnion tissue.

The placental membrane preparation may be combined with prenatal stem cells if desired. For example the preparation may include amniotic fluid cells that are derived from amniotic fluid that is collected during amniocentesis or scheduled C-section from consenting donors. The amniotic fluid is spun thereby pelletizing the amniotic fluid cells. The resulting amniotic fluid cells may be combined with ground placental membrane and cryopreserved in a solution containing approximately 5 to 10% vol/vol Dimethyl Sulfoxide (DMSO) and 15 to 25% vol/vol protein, with the balance being crystalloids.

Minced, ground or morselized membrane particles may be freeze dried and sterilized, or stored in a cryopreservative or hypothermic storage solution, as described herein, allowing the preservation of the viability of some membrane cells. A suitable ground placental membrane preparation, which includes amniotic fluid cells, is sold by NuTech Medical, Inc. of Birmingham, Alabama under the name NuCel™.

The placental membrane preparation may include a processed cartilage selected from the group consisting of a ground cartilage, a minced cartilage, a cartilage paste and combinations thereof. The processed cartilage may be an autograft cartilage, an allograft cartilage or combinations thereof. When processed cartilage is added to a minced or ground placental membrane preparation, the processed cartilage is preferably provided in between a 3:1 and a 1:3 ratio by volume to the original membrane preparation. In an additional embodiment, the minced, ground or morselized membrane particles may have an average particle size of less than about 1.5 mm and are absorbed to a collagen matrix. The collagen matrix may them be used in a method of treating wounds, as will be described in more detail below.

The placental membrane preparation may include hyaluronic acid, saline or a combination thereof. Hyaluronic acid and saline may be included with the placental membrane preparation when it is desired to inject the preparation into a skeletal joint. When hyaluronic acid or saline is added to a placental membrane preparation, the hyaluronic acid or saline is preferably provided in a 2:1 or 1:1 ratio by volume to the original membrane preparation.

The placental membrane preparation may include one or more biocompatible glues. Biocompatible glues are natural polymeric materials that act as adhesives. Biocompatible glues may be formed synthetically from biological monomers such as sugars and may consist of a variety of substances, such as proteins and carbohydrates. Proteins such as gelatin and carbohydrates such as starch have been used as general-purpose glues for many years. Preferably, the biocompatible glue is fibrin glue, such as Tisseel. Fibrin is made up of fibrinogen (lyophilized pooled human concentrate) and may also include thrombin (which may be reconstituted with calcium chloride).

C. The Hypothermic Storage Solution

The membrane may be stored in a hypothermic storage solution allowing the preservation of the viability of the membrane cells. The solution presently described is effective in storing tissues at temperatures above freezing, for instance at a temperature ranging from 0° C. to 20° C. In an additional embodiment, the solution is effective at temperatures ranging between more than 0° C. and less than 10° C. In one exemplary embodiment, the hypothermic storage solution may include a commercially available tissue culture media with appropriate supplements. All components of the solution are chemically defined/cGMP compliant and free of both xeno-derived and human-derived components. In this embodiment, the tissue culture media comprises DMEM. DMEM contains amino acids, salts (calcium chloride, potassium chloride, magnesium sulfate, sodium chloride, and monosodium phosphate) and high concentrations of glucose and vitamins (folic acid, nicotinamide, riboflavin, B12). Additionally, it contains iron and phenol red. DMEM is suitable for most types of cells, including human, monkey, hamster, rat, mouse, chicken, and fish cells. DMEM is commercially available from several providers, for instance Corning, Inc. (Tewksbury MA, Catalog #15-018).

The hypothermic storage solution of the present invention further includes supplementation with appropriate buffers to maintain physiological pH despite changes in carbon dioxide concentration produced by cellular respiration. In one embodiment, the buffer comprises HEPES buffer (4-(2-hydroxyethyl)-1-piperazineethanesulfonic acid), a zwitterionic organic chemical buffering agent. HEPES is widely used in cell culture, largely because it is better at maintaining physiological pH as compared to bicarbonate buffers. The HEPES buffer may be used at a concentration as will be known to one of skill in the art, for example from about 20 mM to 30 mM. In one embodiment, the solution contains a concentration of 25 mM HEPES.

The hypothermic storage solution further includes supplementation with albumin. In one embodiment, the albumin is human plasma albumin. In an additional embodiment, the human plasma albumin is recombinant human albumin (rhA), for instance Cellastim rhA manufactured by InVitria (Junction City, KS). The human plasma albumin may be used at a concentration from about 2.0 g/L to about 3.0 g/L. In one embodiment, the solution contains a concentration of about 2.5 g/L rhA. In another embodiment, the solution contains a concentration of at least 3.0 g/L rhA.

D. Storage of the Placental Membrane

In one embodiment, the invention is directed to a method of storing a prepared placental membrane, the method including placing the membrane in a sterile container including a hypothermic storage solution. In this embodiment, the storage solution contains a commercially available cell culture medium, such as DMEM, HEPES buffer at a concentration between 20 mM to 30 mM and rhA at a concentration between about 2.0 g/L to about 3.0 g/L. In an additional embodiment, the sterile container is sealed with a volume of air in contact with the storage solutions such that the ratio of storage solution and air is between about 2:1 and 5:1 (solution volume: air volume).

In this method, the placental membrane preparation may be stored and transported in the hypothermic storage solution of the present invention. In one embodiment, the membrane and storage solution are placed in a sterile container, such as a jar or tray, and sealed to prevent contamination. A volume of air is included within the sealed container to allow for continued metabolism by the cells within the membrane. The ratio of the volume of storage solution to air may vary, as will be known to one of skill in the art. In one embodiment, this ratio may be between about 2:1 and 5:1 (solution volume: air volume). In another embodiment, the ratio is about 3:1. The container may be positioned and sealed within a second container to provide greater protection from contaminants. For example, the membrane may be hypothermically stored between two sterile nested trays (the "tray-in-tray" configuration) or stored between a sterile jar and a sterile tray (the "jar-in-tray" configuration).

The human albumin contained within the presently described storage solution maintains the viability of the placental membrane cells for an extended period of time. In this embodiment, the placental membrane stored within the hypothermic storage solution exhibits a ratio of live to dead cells after an extended period of storage, as illustrated in Table 1 below.

TABLE 1

Ratio of live to dead cells after extended storage times.

| Ratio of Live Cells to Dead Cells | Hours of Hypothermic Storage |
|---|---|
| >1.5 | 36 |
| >1.0 | 120 |
| >2.0 | 360 |
| >1.5 | 720 |
| >1.0 | 1,000 |

In an additional embodiment, the placental membrane exhibits cell viability in the range of 45% to 85% following one thousand hours of being hypothermically stored in the solution.

In one embodiment, the storage solution of the method significantly increases membrane integrity, reduces osmotic swelling, and retains cell viability over time as compared to solutions that do not contain human albumin. For example, the inclusion of human albumin in the solution preserves the thickness, reduces swelling, reduces damage to the epithelial cell layer and promotes cell retention within the extracellular matrix of the placental membrane. Increasing membrane integrity and preserving cell viability may be accomplished by the addition of an effective amount of human plasma albumin to the hypothermic storage solution. In addition, the human plasma albumin acts to preserve the total protein content of the placental membrane. In one embodiment, the hypothermic storage solution herein described maintains a total protein content of more than about 450 ng of protein per mg of placental membrane following twenty-four hours of being hypothermically stored in the solution. In an additional embodiment, the storage solution maintains a total protein content of more than about 300 ng of protein per mg of placental membrane following one thousand hours of being hypothermically stored in the solution (see FIG. 5E).

In an additional embodiment of the method, the addition of the human plasma albumin acts to maintain activity of tissue inhibiting matrix metalloproteinases (TIMPs) 1, 2 and 4. TIMPs are known inhibitors of matrix metalloproteinases (MMPs), which are responsible for enzymatically breaking down various ECM proteins. Maintenance of TIMP activity, and reduction of extracellular matrix proteins, could act to preserve membrane activity over time. In this embodiment, the placental membrane preserved in the storage solution described herein has a total TIMP 1, 2 and 4 concentration of more than 400 ng per mg of placental membrane following twenty-four hours of storage in the hypothermic storage solution of the invention. In an additional embodiment, the placental membrane preserved in the storage solution described herein has a total TIMP 1, 2 and 4 concentration of more than 250 ng per mg of placental membrane following one thousand hours of storage in the hypothermic storage solution of the invention (see FIG. 5F, described herein).

In an additional embodiment, the placental membrane of the method may be minced, ground or morselized prior to storage in the hypothermic storage solution, as described herein, allowing the preservation of the viability of some membrane cells. Additionally, the placental membrane preparation may further include a processed cartilage selected from the group consisting of a ground cartilage, a minced cartilage, a cartilage paste and combinations thereof. The processed cartilage may be an autograft cartilage, an allograft cartilage or combinations thereof. When processed cartilage is added to a minced or ground placental membrane preparation, the processed cartilage is preferably provided in between a 3:1 and a 1:3 ratio by volume to the original membrane preparation. In an additional embodiment, the minced, ground or morselized membrane may be arranged in particles with a size of less than about 1.5 mm and absorbed to the collagen matrix before storage in the hypothermic storage solution. The collagen matrix may them be used in a method of treating wounds, as will be described in more detail below. In addition, the placental membrane tissue is at least partially submerged in the storage solution including DMEM and at least about 0.025% w/v human plasma albumin.

In an additional embodiment, the invention includes a system comprising a placental membrane hypothermically stored within a container. The container includes a hypothermic storage solution including a commercial available tissue culture medium supplemented with human plasma albumin and an appropriate buffer to maintain physiological pH. In one embodiment, the human plasma albumin is recombinant human albumin at a concentration from about 2.0 g/L to about 3.0 g/L. In one embodiment, the solution contains a concentration of about 2.5 g/L rhA. In another embodiment, the solution contains a concentration of at least 3.0 g/L rhA. In this embodiment, the buffer comprises HEPES buffer at a concentration from about 20 mM to 30 mM. In one embodiment, the solution contains HEPES at a concentration of 25 mM.

The sterile container for holding the placental membrane and the solution may be sealed to prevent contamination. A volume of air is included within the sealed container to allow for continued metabolism by the cells within the membrane. The ratio of the volume of storage solution to air may vary, as will be known to one of skill in the art. In one embodiment, this ratio may be between about 2:1 and 5:1 (solution volume: air volume). In another embodiment, the ratio is about 3:1. The container may be positioned and sealed within a second container to provide greater protection from contaminants. The system may further include HEPES buffer as a component of the storage solution, where the HEPES buffer is at a concentration between 20 mM and 30 mM.

The human albumin contained within the presently described storage solution of the system maintains the viability of the placental membrane cells for an extended period of time. In this embodiment, the placental membrane stored within the hypothermic storage solution exhibits a ratio of live to dead cells after an extended period of storage, as illustrated in Table 1. In an additional embodiment, the inclusion of human albumin in the solution preserves the thickness, reduces swelling, reduces damage to the epithelial cell layer and promotes cell retention within the extracellular matrix of the placental membrane by significantly increasing membrane integrity, reducing osmotic swelling, and retaining cell viability over time as compared to solutions which do not contain human albumin. The human plasma albumin acts to preserve the total protein content of the placental membrane. In one embodiment, the hypothermic storage solution of the system maintains a total protein content of more than about 450 ng of protein per mg of placental membrane following twenty-four hours of being hypothermically stored in the solution. In an additional embodiment, the storage solution included in the system maintains a total protein content of more than about 300 ng of protein per mg of placental membrane following one thousand hours of being hypothermically stored in the solution (see FIG. 5E).

In another embodiment, the addition of the human plasma albumin to the storage solution of the system acts to maintain activity of TIMPS 1, 2 and 4. In this embodiment, the placental membrane preserved in the storage solution of the system has a total TIMP 1, 2 and 4 concentration of more than 400 ng per mg of placental membrane following twenty-four hours of storage. In an additional embodiment, the placental membrane preserved in the storage solution of the system has a total TIMP 1, 2 and 4 concentration of more than 250 ng per mg of placental membrane following one thousand hours of storage (see FIG. 5F, described herein).

The placental membrane preparation included in the system may include a processed cartilage selected from the group consisting of a ground cartilage, a minced cartilage, a cartilage paste and combinations thereof, as described in detail above. In an additional embodiment, the minced, ground or morselized membrane particles may have an average particle size of less than about 1.5 mm and may then be absorbed to a collagen matrix. In addition, the placental membrane of the system may be meshed so that it may be stretched to increase its length and width. The membrane of the system may comprise both the amniotic and chorionic layers. The spongy layer of the amnion tissue may be removed or may remain intact depending on the intended application for the preserved tissue. In another example, the chorion of the placental membrane has been removed. In another example, the epithelial layer has been removed from the placental membrane.

E. Treatment of Wounds and Defects

The embodiments of the placental membrane preparation, described herein, may be used to regenerate damaged tissues. The storage solution and methods may be utilized with placental membranes used in a number of clinical conditions including, but not limited to, traumatic injury, such as lacerations or burns.

The placental membrane in the hypothermic storage solution may act as a scaffold or matrix for cell engraftment and in-growth. Thus, the preserved membranes may act as an integral matrix with cells intact in their normal location and without culturing. The placental membranes also provide a reservoir of growth factors attracting incoming blood-born MSCs, chondrocytes, and other reparative cells.

In one embodiment, the present invention includes a method for treating a wound comprising the application of the placental membrane tissue stored as described above to a wound. In certain embodiments, the placental membrane comprises an amniotic membrane. Here, the stromal surface of the tissue is applied to the wound to promote healing. Alternatively, the membrane tissue may comprise cartilage.

In an additional embodiment, the placental membrane may be ground, minced or morselized using techniques known in the art, prior to hypothermically storing the placental membrane in the storage solution. Such membranes may be further combined with ground or minced autograft or allograft cartilage for implantation into the wound or defect.

In an additional embodiment, the placental membrane may be stored within the hypothermic solution for an extended period of time without freezing the membrane. In this embodiment, the membrane is not frozen prior to or after being hypothermically stored in the solution.

In a further embodiment, the present invention is directed to a system for treating a wound comprising a placental membrane hypothermically stored within a container. The system includes a storage solution of DMEM and human plasma albumin. In an additional embodiment the human plasma albumin is recombinant human albumin. The placental membrane of the system exhibits ratios of live to dead cells after extended storage times as illustrated in Table 1. In an additional embodiment, the addition of the human plasma albumin to the solution within the system acts to maintain activity of TIMPs 1, 2 and 4. TIMPs are known inhibitors of MMPs, which are responsible for enzymatically breaking down various ECM proteins. Maintenance of TIMP activity, and reduction of extracellular matrix proteins, could act to preserve membrane activity over time.

In an additional embodiment, the placental membrane within the system may be ground, minced or morselized using techniques known in the art, prior to hypothermically storing the placental membrane in the storage solution. Such membranes may be further combined with ground or minced autograft or allograft cartilage for implantation into a defect.

EXPERIMENTAL

A. Definitions

"Cell Viability" is defined as the percentage of surviving cells out of total cells in a cell suspension. Defined as $$V = \frac{L}{(L+D)} * 100\%,$$

where V is the viability percentage, L is the number live cells, and D is the number of dead cells in a suspension.

"H&E stain" is defined as hematoxylin and eosin stain.

"Modulus" is defined as the extent to which an object resists deformation in response to an applied force. Defined as $$M = \frac{\sigma}{e}.$$

"Strain" is defined as the normalized measure of deformation defined as the change in length divided by the original length; e=ΔL/L.

"Stress" is $$\sigma = \frac{F}{A},$$

defined as where F is the force (N) acting on the area (A, cm$^2$)

"Total Protein Content" is defined as the total level of 40 known cytokines. To remove bias, protein levels were normalized by tissue weight. Levels are defined as $$T = \sum_{Protein\,1}^{Protein\,40} \frac{P_n}{W}$$

where T is the total protein content, P is the concentration of each protein, and W is the weight of the tissue sample.

B. Preliminary Cell Viability Study

Preliminary studies evaluating storage of amniotic membrane in hypothermic conditions were performed using the following groups:

(1) Cellgenix CellGro
(2) Hypothermosol
(3) RPMI
(4) DMEM (containing 25 mM HEPES buffer)
(5) fully-supplemented DMEM (containing 25 mM HEPES Buffer, Insulin, Transferrin, Selenium, 2 mM L-glutamine, and 0.25% w/v rhA)
(6) DMEM (containing 25 mM HEPES buffer and 0.25% w/v rhA).

Figure 1B:
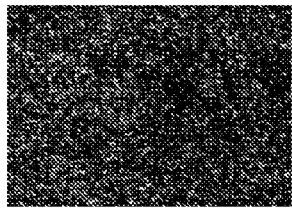
FIG. 1B is a quantitative image of cell viability.
Figure 1C:
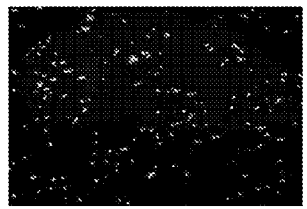
FIG. 1C is an additional quantitative image of cell viability.
Figure 1D:
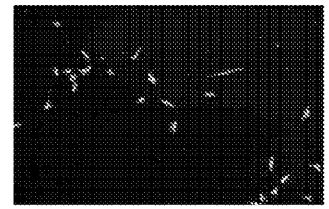
FIG. 1D is an additional quantitative image of cell viability.

In this preliminary study, a Multitox Fluor Viability kit was used to determine live cell viability over time to serve as an indication of membrane integrity. FIG. 1A illustrates the results, graphed as a ratio of Multitox live cells to total DNA count (as determined by a Picogreen dsDNA assay). The DMEM+recombinant human albumin (rhA) solution was most effective at retaining cell viability over time. FIGS. 1B-1D illustrate qualitative imaging of the three conditions with the best viability at their endpoints. As illustrated in these images, the DMEM+rhA solution has considerable viability at 42 days. These results show that the hypothermic storage solution containing DMEM+rhA demonstrates superior viability as compared to the other storage media.

C. Cell Viability as a Measure of Membrane Integrity

1. Multitox Assay

In this experiment cell viability was used as a measure for membrane integrity. Preliminary data suggested that DMEM+rhA would be the best combination for preserving membrane integrity. DMEM alone and DMEM+rhA contained within (a) a "jar-in-tray" or (b) "tray-in-tray" arrangement were investigated. Similar oxygen to storage media ratios were maintained for both groups. Therefore, the main variable between storage conditions was the volume of storage media used. The "jar-in-tray" configuration allowed for a storage solution volume of 12 mL of media in a 15 cc jar, while the "tray-in-tray" configuration allowed for a significantly higher volume of storage media 30 mL of media in a 40 cc tray.

Figure 2A:
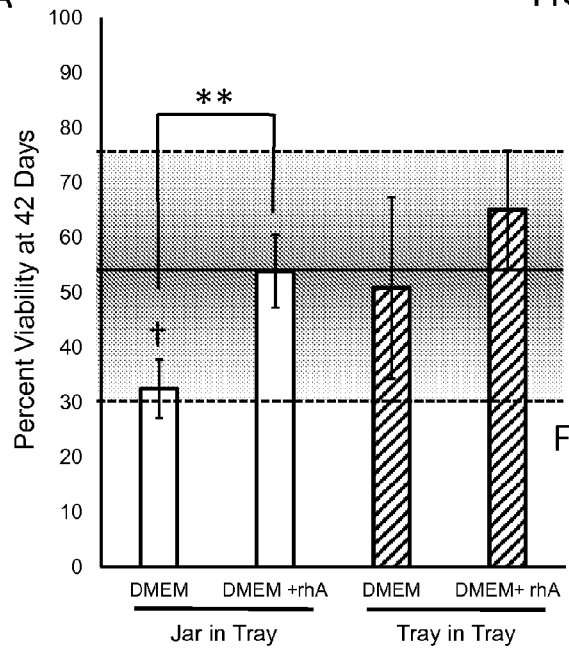
FIG. 2A is a graph showing the viability of placental membrane cells at 42 days.
Figure 2B:
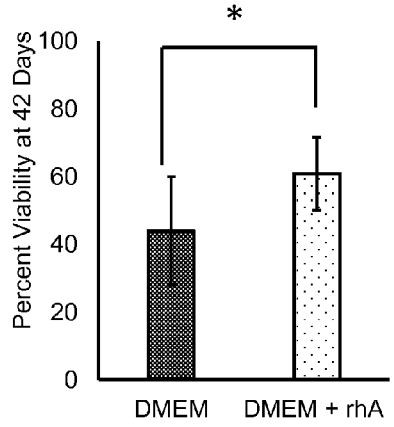
FIG. 2B is an additional graph showing the viability of placental membrane cells at 42 days.
Figure 2C:
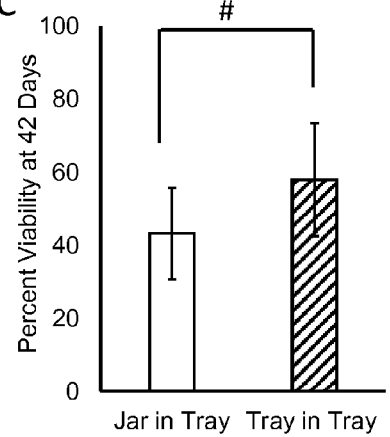
FIG. 2C is an additional graph showing the viability of placental membrane cells at 42 days.

At days 1 and 42 membranes stored in the different storage media and packaging configurations were subjected to a PBS rinse followed by digestion in collagenase to free the cells from the membrane. The cells were then directly assessed for viability using the Multitox viability assay. FIG. 2A illustrates the viability of cells isolated from placental membranes harvested from four donors. The solid black line at approximately 55% viability indicates the average viability at day 1, while the broken lines and shaded area indicate the standard deviation. Several trends were evident in evaluating this data. The data demonstrates that DMEM+rhA retained higher cell viability than DMEM alone across both storage conditions and the "Tray-in-Tray" configuration trended towards higher viability as compared to the "Jar-in-Tray" configuration. The membrane stored in DMEM+rhA solution in the "Tray-in-Tray" configuration retained the highest amount of viability at 42 days. The "Tray-in-Tray" and "Jar-in-Tray" samples were combined to evaluate whether there was a significant difference between the storage conditions. FIG. 2B illustrates that the DMEM+rhA solution had significantly higher viability than DMEM alone. There was a significant difference between the two packaging conditions with the "Tray-in-Tray" configuration resulting in significantly higher viability than the Jar in Tray configuration, likely due to a higher volume of storage media (FIG. 2C).

2. Cell Imaging

Figure 3:
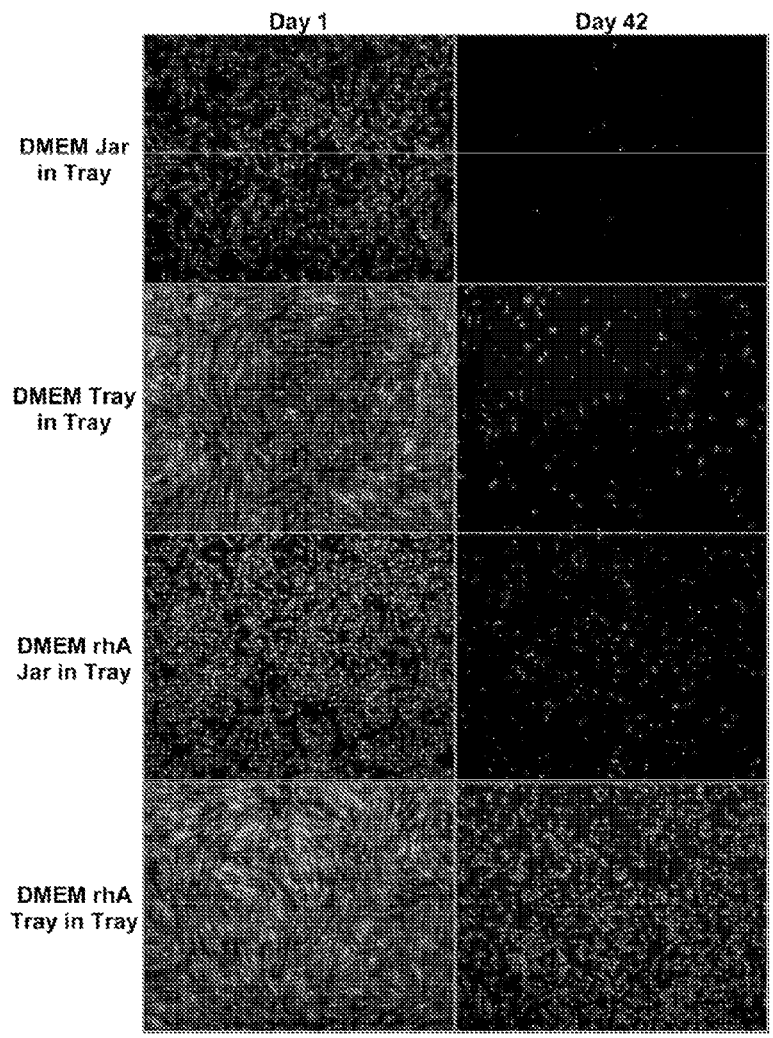
FIG. 3 is an illustration of qualitative assessment of cell viability over time.
Figures 4A, 4B:
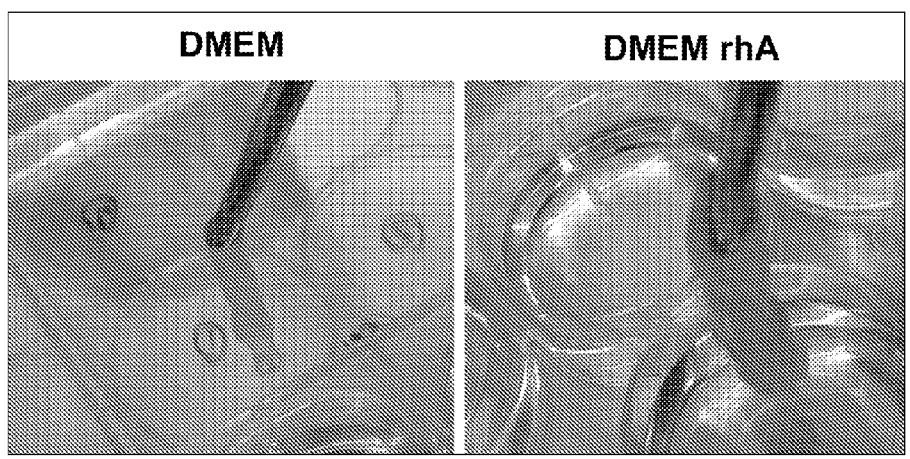
FIG. 4A is an illustration of the macroscopic handling characteristics of tissue stored in a DMEM solution.
FIG. 4B is an illustration of the macroscopic handling characteristics of tissue stored in a DMEM+recombinant human albumin (rhA) solution.

As a secondary measure to verify cell viability post membrane digestion at 42 days of storage, cells remaining after the Multitox viability testing were seeded onto a 24-well plate and cultured (37° C., 5% $CO_2$) in standard growth media (DMEM with 1% Penicillin, 1% Streptomycin, and 1% Amphotericin, 2 mM L-glutamine, and 20% FBS). After 48-72 hours, cells were stained using Calcein AM and imaged under a fluorescent microscope to qualitatively analyze cell viability. The trends from the multitox viability studies held true for qualitative evaluation of cell density after 42 days of hypothermic storage. Specifically, it was demonstrated that at Day 42, the "Tray-in-Tray" packaging configuration exhibited improved viability over the "Jar-in-Tray" packaging configuration and the DMEM+rhA solution exhibited improved cell viability over DMEM alone (FIG. 3).

D. H&E Staining and Microscopic Inspection of Membrane Integrity

In addition to quantitative comparisons of membrane integrity, macroscopic handling characteristics were assessed and H&E staining was performed to evaluate preservation of membrane integrity after extended periods of hypothermic storage. Some qualitative handling characteristics of amniotic membrane samples stored for 42 days were: (1) samples in DMEM+rhA were consistently thicker and more like tissue at 1 day; and (2) amniotic membrane samples stored in DMEM alone seemed thinner.

To more closely examine membrane integrity, amniotic membrane stored in DMEM or DMEM+rhA for 4 or 6 weeks were cross sectioned and stained with hematoxylin and eosin (H&E). Of note, 4 and 6 week staining of amniotic membrane was done at different times; therefore, the staining intensity varies between 4 and 6 week samples. There were clear differences in the amniotic membranes stored in DMEM (FIGS. 5A and 5C) and those stored in DMEM+rhA (FIGS. 5B and 5D) at both 4 and 6 week time points. These differences included: (1) more damage to epithelial layer of membranes stored in the DMEM solution alone; (2) the thickness of the amniotic membrane was preserved more efficiently in membranes stored in the DMEM+rhA solution; and (3) more cells were retained within the ECM of amniotic membranes stored in the DMEM+rhA solution. Overall, tissues stored in the DMEM+rhA solution appeared larger and thicker as compared to tissues stored in DMEM only.

E. Proteomics Assay to Evaluate Protein Content

Total protein content of the stored placental membrane cells was next assessed to determine whether storage conditions affected the growth factor content of the membranes over time. Membrane tissues were weighed at predetermined time points. The tissues were then cryo-homogenized and total protein content was extracted using a total protein extraction buffer. Total protein was then measured using a custom quantibody microarray to quantitatively assess 40 separate cytokines simultaneously for each sample. For each sample, the levels of all 40 cytokines were summed and normalized by the sample weight to determine the total amount of protein in picograms per milligram of membrane (FIG. 5E), with each condition assessed in duplicate.

According to the proteomics data means, trends similar to those seen with histology, cell viability, and cell viability imaging were observed. The concentrations of tissue inhibiting TIMPs 1, 2, and 4 were summed for each sample and averaged for each storage solution condition (FIG. 5F).

TIMPs are known inhibitors of MMPs, which are responsible for enzymatically breaking down various ECM proteins. Overall, it appears that maintenance of TIMP activity could be a potential mechanism for the preservation of membrane integrity over time.

F. Mechanical Testing to Evaluate Membrane Integrity

Figures 6A, 6B, 6C:
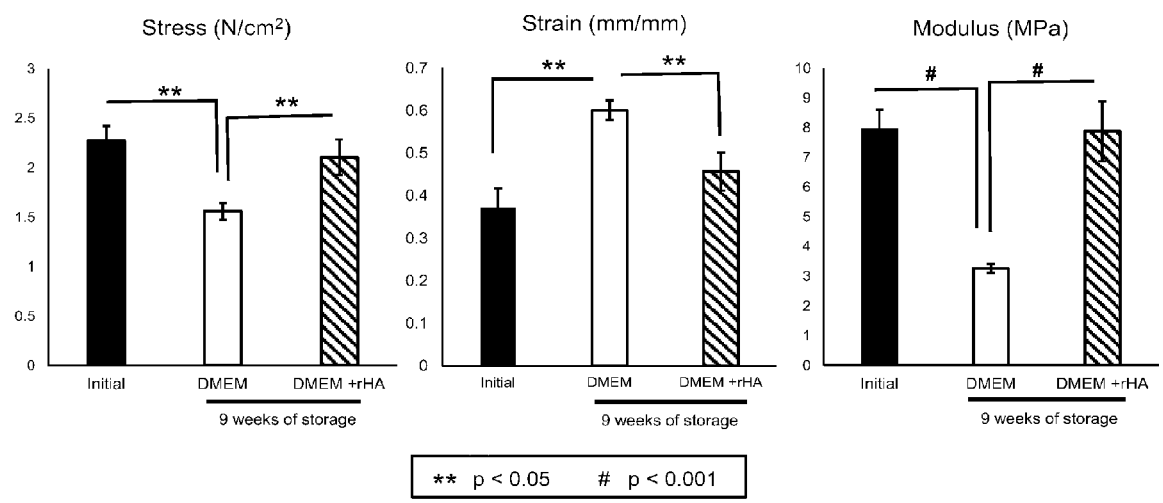
FIG. 6A is a graph illustrating stress testing on cells incubated in the storage solution for nine weeks.
FIG. 6B is a graph illustrating strain testing on cells incubated in the storage solution for nine weeks.
FIG. 6C is a graph illustrating modulus testing on cells incubated in the storage solution for nine weeks.

Mechanical testing was completed on samples stored in the DMEM storage solution at Day 1. These values were compared to data collected for membranes stored in DMEM and DMEM+rhA at 9 weeks. Briefly, an MTS was used to report the time, displacement, and force every 1/100th of a second. The maximum values for force and the maximum displacement were calculated at the time of membrane failure. Using the maximum displacement and the initial distance between the clamps, strain was calculated: e=(Lf−Li)/Li (FIG. 6B). Stress is defined as and was calculated using maximums from the data collected during tensile testing (FIG. 6A). Finally, the modulus of elasticity ('Modulus'=stress/strain) is the mathematical description of an object's tendency to be deformed elastically when a force is applied to it (FIG. 6C).

Stress, strain and modulus were calculated and evaluated for all data points. Interestingly, for all mechanical properties there were significant differences between the amniotic membrane samples stored in the DMEM solution and those stored in DMEM+rhA solution. Additionally, amniotic membrane samples hypothermically stored in the DMEM+rhA solution were not significantly different in their mechanical properties compared to mechanical properties of amniotic membrane at day 1. The cells stored in the DMEM+rhA solution were able to sustain the largest stress, underwent less strain, and had a greater modulus than those stored in the DMEM solution. Importantly, these characteristics matched what was seen in tissue stored for only 1 day. These results imply that samples stored in DMEM+rhA had less tissue degradation than those stored in DMEM alone. These data suggest that the DMEM+rhA storage solution results in less destruction and/or better preservation of the membrane than DMEM alone.

CONCLUSION

All tests performed indicate that the integrity of the amniotic membrane when subjected to hypothermic storage conditions is best preserved when using the DMEM+rhA solution compared to DMEM solution. This conclusion is supported by data from cell viability studies, H&E staining, proteomics microarrays, and mechanical testing.

G. Animal Studies

Experimental

Placental membrane samples were examined for their effectiveness in promoting wound healing. Four 15 mm diameter, full thickness wounds were created on the dorsal skin surface (i.e. the back) of three laboratory rats. Four types of placental membrane preparations were placed stromal side down on the wounds of each animal—one type of membrane on each wound. The following types of membranes were utilized:

(1) Fresh placental membrane stored in a hypothermic solution containing DMEM, 25 mM HEPES and 2.5 g/L rhA after 25 days storage;
(2) Dehydrated meshed placental cell preparation;
(3) Dehydrated fully intact amnion; and
(4) Control (no membrane)

A primary dressing (cuticerin) was secured to the skin using staples to cover the wounds.

The wounds were inspected nine and twenty-one days post-procedure and histological samples of the wounds were collected and evaluated for wound healing.

Results

Figure 7A:
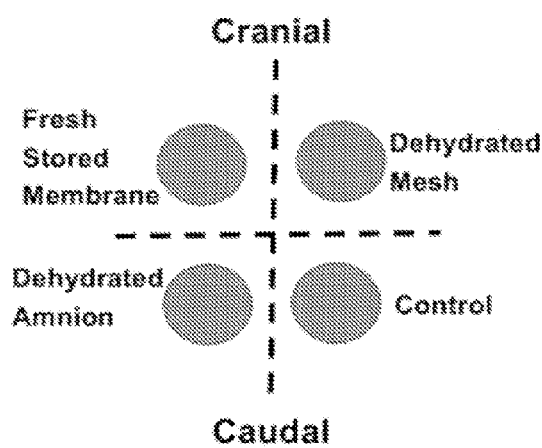
FIG. 7A is a guide illustrating the placement of the experimental placental membranes over wounds.
Figure 7B:
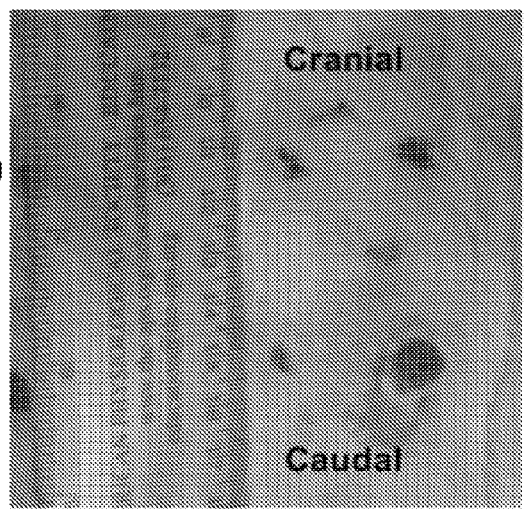
FIG. 7B is an illustration of wounds treated with experimental placental membranes nine days post-procedure.
Figure 7C:
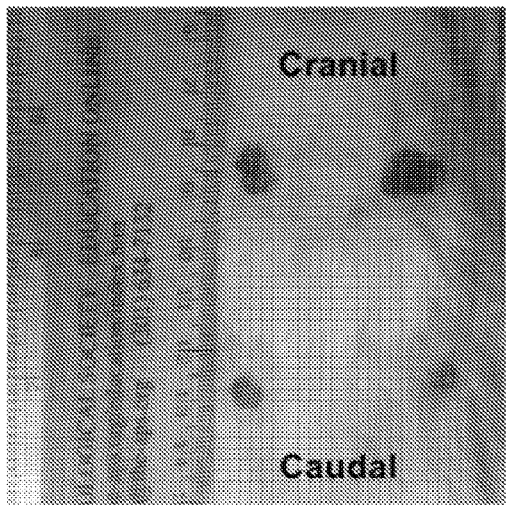
FIG. 7C is an additional illustration of wounds treated with experimental placental membranes nine days post-procedure.
Figure 7D:
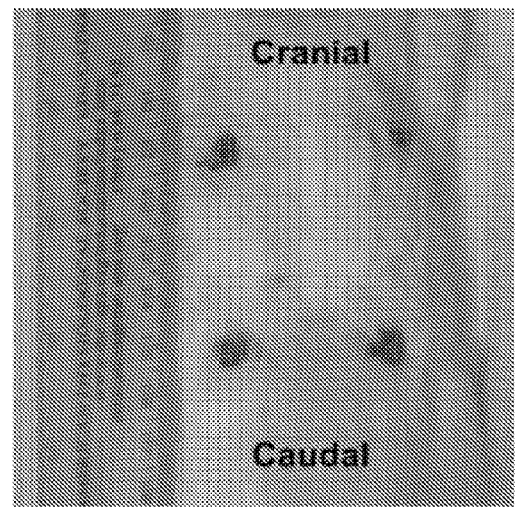
FIG. 7D is an additional illustration of wounds treated with experimental placental membranes nine days post-procedure.
Figure 9A:
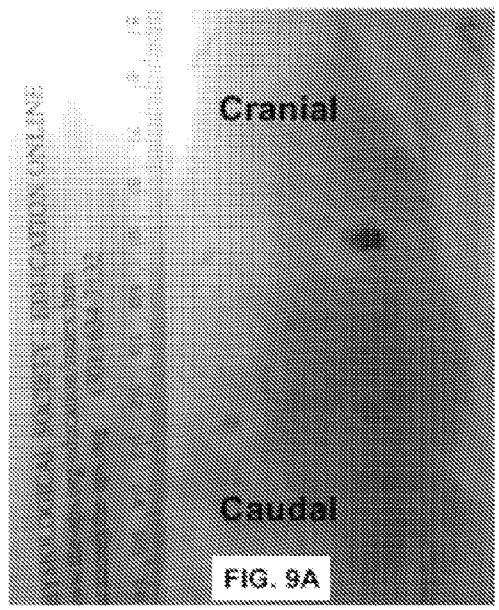
FIG. 9A is an illustration of wounds treated with experimental placental membranes twenty-one days post-procedure.
Figure 9B:
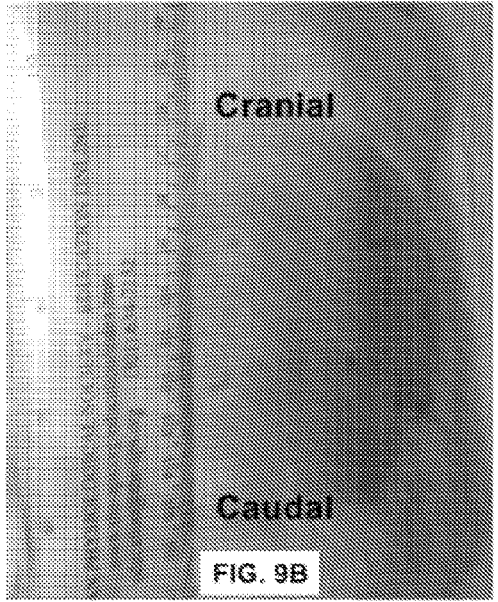
FIG. 9B is an additional illustration of wounds treated with experimental placental membranes twenty-one days post-procedure.
Figure 9C:
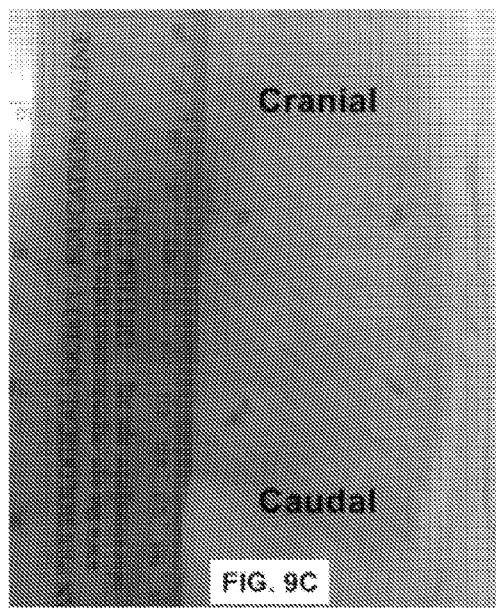
FIG. 9C is an additional illustration of wounds treated with experimental placental membranes twenty-one days post-procedure.
Figure 9D:
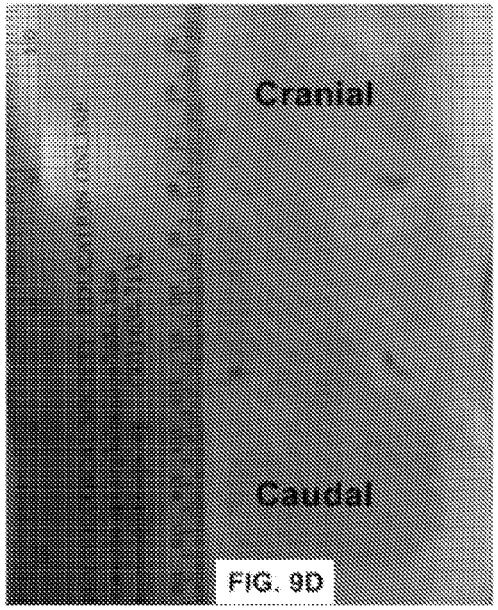
FIG. 9D is an additional illustration of wounds treated with experimental placental membranes twenty-one days post-procedure.
Figure 13A:
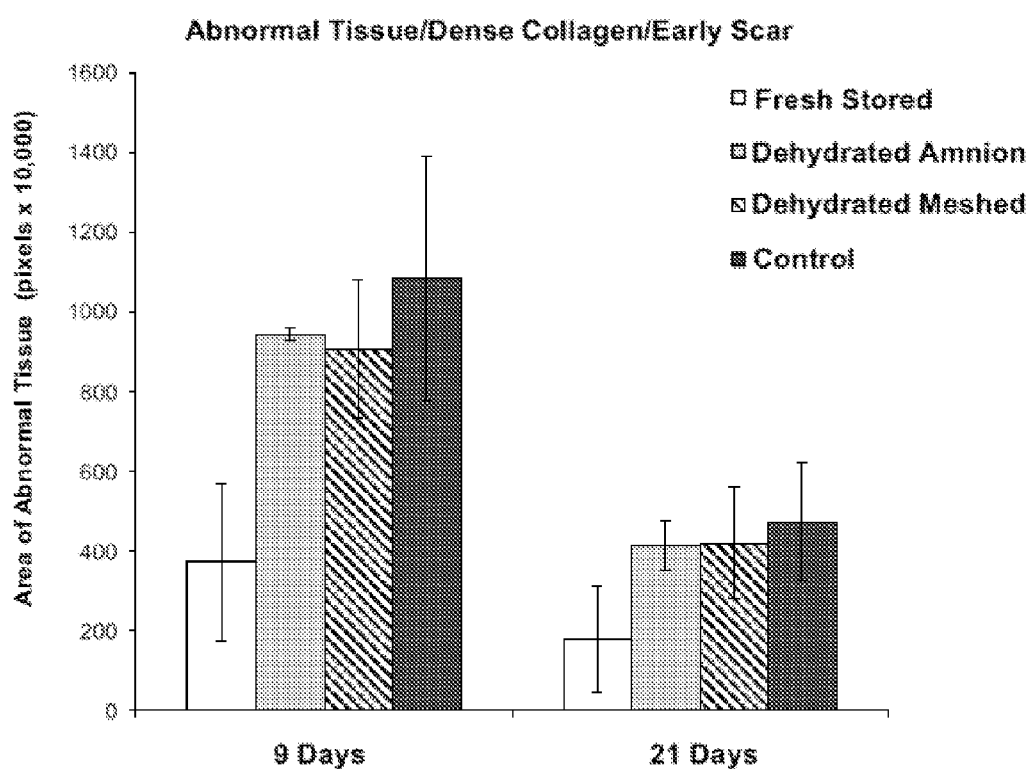
FIG. 13A is a quantification of abnormal tissue in wounds treated with experimental placental membranes at nine and twenty-one days post-procedure.
Figure 13B:
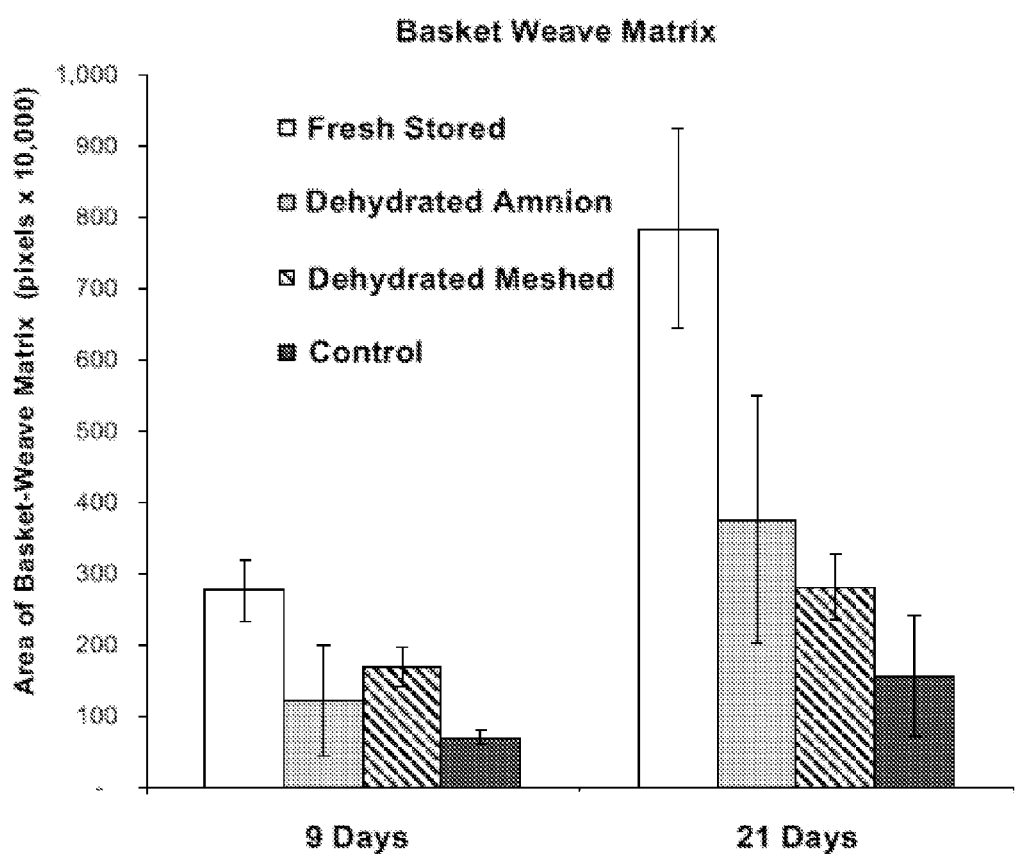
FIG. 13B is a quantification of basket-weave matrix in wounds treated with experimental placental membranes at nine and twenty-one days post-procedure.
Figure 13C:
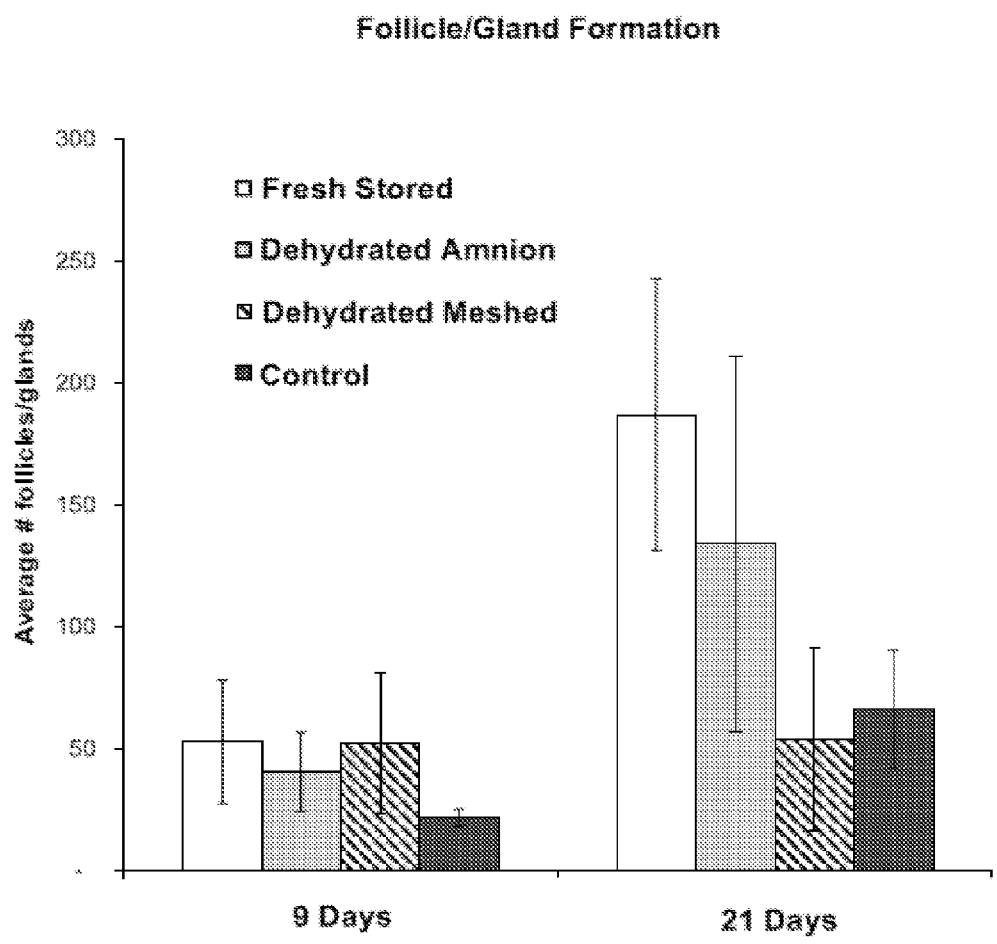
FIG. 13C is a quantification of follicle/gland formation in wounds treated with experimental placental membranes at nine and twenty-one days post-procedure.

Nine days post-procedure the wounds treated with the fresh stored membrane, dehydrated mesh and dehydrated amnion appeared smaller than those of the control group (FIGS. 7B-7D). FIG. 7A provides a guide indicating placement of the membranes on the wounds. Referring now to FIG. 8, histological examination indicates that the wounds treated with the fresh stored membrane and the dehydrated mesh samples showed more cellular granulation tissue and re-epithelialization as compared to the control. Specifically, referring to FIG. 13A, the wounds treated with fresh stored membrane exhibited substantially less abnormal tissue compared to wounds treated with dehydrated mesh, dehydrated amnion, and control. Conversely, referring to FIG. 13B, the wounds treated with fresh stored membrane exhibited greater basket-weave matrix than the other three treatment groups, although the number of follicles and sebaceous glands in wounds treated with fresh stored membrane were not significantly different than the other treatment groups at nine days (FIG. 13C).

Twenty-one days post-procedure the wounds treated with the fresh stored membrane were smaller as compared to the wounds of the dehydrated mesh, dehydrated amnion, and control groups (FIGS. 9A-9D). The results of the 21-day post-procedure histological examination are illustrated in FIGS. 10-12. As shown in FIG. 10, the wound treated with fresh stored placental membrane showed increased wound healing as compared to the other samples. Referring to FIG. 11C, the histological testing of the untreated wound illustrated granulation tissue and a thin area of epithelialization. The wounds treated with the dehydrated mesh (FIG. 11D) and the dehydrated amnion (FIG. 11A) preparations showed only slightly increased granulation and epithelialization as compared to the control. In contrast, the wound treated with the fresh stored placental membrane (FIG. 11B) illustrated increased collagen deposition and the extensive development of hair follicles and sebaceous glands. These changes are an indication of scarless regenerative wound healing. FIG. 12D illustrates this increased development of hair follicles and sebaceous glands as well as new collagen deposition and the formation of granulation tissue in the wound treated with the fresh stored placental membrane. In contrast, these developments are not present in the wounds treated with the control (FIG. 12A), the dehydrated mesh (FIG. 12B) or the dehydrated amnion (FIG. 12C) preparations. Further, referring to FIG. 13A, although all treatment groups exhibited less abnormal tissue at twenty-one days compared with nine days, the wounds treated with fresh stored membrane continued to exhibit less abnormal tissue compared to wounds treated with dehydrated mesh, dehydrated amnion, and control. Similarly, referring to FIG. 13B, although the wounds of all treatment groups exhibited greater basket-weave matrix, the wounds treated with fresh stored membrane exhibited greater basket-weave matrix than the other three treatment groups. Unlike at nine days, at twenty-one days, the wounds treated with fresh stored membrane exhibited a greater number of follicles and sebaceous glands than in wounds treated with dehydrated mesh and control (FIG. 13C).

CONCLUSION

It is clear from the representative histological images (FIGS. 10-12) and from the quantification thereof (FIGS. 13A-13C) that treatment of the wound with the fresh stored placental membrane scaffold resulted in the best skin regeneration response as compared to the dehydrated amnion and dehydrated mesh preparations. The wounds treated with the fresh stored membrane showed evidence of re-epithelialization at nine days. The epithelial layer in these wounds developed into a thick stratified epidermis with finger-like projections that extended into the dermal layer, representative of a healthy epidermal healing. In contrast, the other preparations showed only limited re-epithelialization across the wound bed at nine days post-procedure.

Blood vessel presence appeared to be greater at the nine day time point as compared to the twenty-one day time point for all groups. The dehydrated amnion appeared to provide the highest level of vessel formation. It is apparent that the tissue was being remodeled and the vessels were breaking down as the wound healing process progressed.

These data suggest that the fresh, hypothermically stored placental membranes expedited the wound healing process. Further, the fresh stored grafts enhanced the body's ability to regenerate skin tissue that closely mimics unwounded skin. This is apparent by the early epidermal, hair follicle and gland formation, as well as the high degree of basket weave matrix. The fresh hypothermically stored placental preparations illustrated a strikingly greater response in wound healing.

What is claimed is:

1. A method for treating a wound comprising:
hypothermically storing a placental membrane in a container including a solution including Dulbecco's modified Eagle's medium (DMEM) and human plasma albumin,
wherein the human plasma albumin promotes cell viability and membrane integrity of the placental membrane,
storing the placental membrane in the solution for at least 14 days before applying the placental membrane to a wound,
removing the placental membrane from the container, and applying the placental membrane to the wound.

2. The method according to claim 1 comprising applying a stromal-side of the placental membrane to the wound.

3. The method according to claim 1 comprising processing the placental membrane into placental membrane pieces prior to storing the placental membrane in the container.

4. The method according to claim 3 wherein the placental membrane pieces have particle sizes ranging from 0.1 mm to 5 mm.

5. The method according to claim 1 comprising applying the placental membrane to the wound in combination with amniotic fluid cells.

6. The method according to claim 1 comprising applying the placental membrane to the wound in combination with cartilage pieces.

7. The method according to claim 6 comprising applying the cartilage pieces and the placental membrane to the wound in a 3:1 to 1:3 ratio by volume.

8. The method according to claim 1 wherein the placental membrane exhibits a ratio of live cells to dead cells greater than 2.0 following three hundred sixty hours of being hypothermically stored in the solution.

9. The method according to claim 1 wherein the placental membrane exhibits a ratio of live cells to dead cells of greater than about 1.5 following seven hundred twenty hours of being hypothermically stored in the solution.

10. The method according to claim 1 wherein the placental membrane exhibits a cell viability in a range between about 45% and 85% following one thousand hours of being hypothermically stored in the solution.

11. The method according to claim 1 comprising morselizing the placental membrane and adsorbing the morselized placental membrane to a mammalian collagen matrix prior to hypothermically storing the placental membrane in the solution.

12. The method according to claim 1 comprising meshing the placental membrane prior to hypothermically storing the placental membrane in the container.

13. The method according to claim 1 comprising stretching the meshed placental membrane prior to applying the meshed membrane to the wound.

14. The method according to claim 1 wherein the wound is a burn.

15. The method according to claim 1 wherein the wound is a laceration.

16. The method according to claim 1 wherein the placental membrane includes no placental membrane-derived cultured cells.

* * * * *